United States Patent
Hamprecht et al.

[11] Patent Number: 6,107,253
[45] Date of Patent: Aug. 22, 2000

[54] 1-(PYRIDYL)-PYRAZOLS AND THEIR USE AS HERBICIDES

[75] Inventors: Gerhard Hamprecht, Weinheim; Elisabeth Heistracher, Ludwigshafen; Ralf Klintz, Gruenstadt; Peter Schäfer, Ottersheim; Cyrill Zagar, Ludwigshafen; Helmut Schiffer, Mutterstadt; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/011,633

[22] PCT Filed: Aug. 7, 1996

[86] PCT No.: PCT/EP96/03493

§ 371 Date: Feb. 12, 1998

§ 102(e) Date: Feb. 12, 1998

[87] PCT Pub. No.: WO97/07114

PCT Pub. Date: Feb. 27, 1997

[30] Foreign Application Priority Data

Aug. 21, 1995 [DE] Germany ............................ 195 30 606

[51] Int. Cl.⁷ ......................... A01N 43/40; C07D 401/04
[52] U.S. Cl. .................. 504/253; 546/275.4; 546/276.1
[58] Field of Search ............................. 546/275.4, 276.1; 504/253

[56] References Cited

U.S. PATENT DOCUMENTS

| | | | |
|---|---|---|---|
| 4,580,905 | 4/1986 | Schwitters et al. | 366/149 |
| 4,747,867 | 5/1988 | Gehring et al. | 548/377 |
| 4,772,312 | 9/1988 | Schallner et al. | 546/2 |
| 4,804,398 | 2/1989 | Gehring et al. | 548/377 |
| 5,167,691 | 12/1992 | Maravetz | 548/372.1 |
| 5,198,014 | 3/1993 | Maravetz | 504/225 |
| 5,306,694 | 4/1994 | Phillips et al. | 504/253 |

FOREIGN PATENT DOCUMENTS

| | | |
|---|---|---|
| 204 242 | 12/1986 | European Pat. Off. . |
| 34 08 727 | 9/1984 | Germany . |
| 35 20 327 | 12/1986 | Germany . |
| 35 20 330 | 12/1986 | Germany . |
| 2 136 427 | 9/1984 | United Kingdom . |

OTHER PUBLICATIONS

Derwent Abst DE 3520–327.
Chem. Abst. vol. 113, 1990, CA 113:167389.

*Primary Examiner*—Jane Fan
*Attorney, Agent, or Firm*—Keil & Weinkauf

[57] ABSTRACT

Substituted 1-(pyridyl)pyrazoles of the formula I

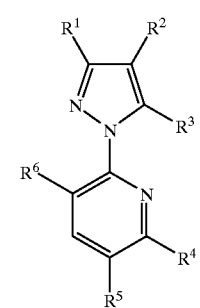

where the substituents have the meanings set forth in the specification, and the N-oxides and the agriculturally utilizable salts of the compounds I, processes for their preparation and their use as herbicides.

6 Claims, No Drawings

1-(PYRIDYL)-PYRAZOLS AND THEIR USE AS HERBICIDES

This is a 371 of PCT/EP96/03493, Aug. 7, 1996 now WO 97/07114, Feb. 27, 1997.

The present invention relates to new 1-(pyridyl) pyrazoles, processes for their preparation and their use as herbicides.

It has already been disclosed that certain 1-(pyridyl) pyrazoles, eg. 4-cyano-5-amino-1-(3-chloro-5-trifluoromethyl-2-pyridyl)pyrazole (German Offenlegungsschrift 3 408 727), 4-nitro-5-amino-1-(3-chloro-5-trifluoromethyl-2-pyridyl)pyrazole, 4-ethoxycarbonyl-5-amino-1-(3-chloro-5-trifluoromethyl-2-pyridyl)pyrazole (German offenlegungsschrift 3 520 330), and further derivatives described there, 4-cyano-5-n-propylamino-1-(3,5-dichloro-2-pyridyl)pyrazole (DE 3 520 327), 4-chloro-5-methylsulfonyl-1-(3-chloro-5-trifluoromethyl-2-pyridyl) pyrazole (JO 2142- 785) and also 5-cyano-1-(2-pyridyl)-N-methylpyrazole-4-carboxamide (U.S. Pat. No. 4,580,905) have herbicidal properties. 5-Amino-3-cyano-4-trifluoromethylsulfonyl-1-(3-chloro-5-trifluoromethyl-2-pyridyl)pyrazole has insecticidal properties (EP 500 209).

The herbicidal action of the known compounds with respect to weeds, however, is not always completely satisfactory. The object of the present invention was accordingly to prepare novel herbicidally active compounds with which undesired plants can be specifically controlled better than hitherto.

U.S. Pat. No. 5,198,014 describes 3-(4-cyano-1-(3-chloro-5-trifluoromethyl-2-pyridyl)-5-pyrazolyl)acrylic acid (Example 4, compound No. 14, Table 3) and the chloro compound correspondingly substituted in the pyridine 6-position (No. 19, Table 3). As the comparison of the herbicidal action shows, the pyridine-6-H compound 14 has a significantly stronger herbicidal action than the pyridine-6-Cl compound 19.

It has now surprisingly been found that novel substituted 1-(pyridyl)pyrazoles of the general formula I

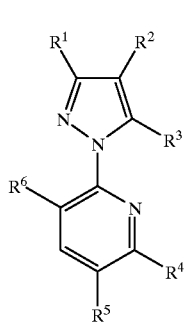

I where the substituents have the following meanings:
$R^1$ is hydrogen, $C_1$–$C_3$-alkyl, halogen, $C_1$–$C_3$-haloalkyl;
$R^2$ is $C_1$–$C_4$-alkyl, $C_2$–$C_4$-alkenyl, $C_2$–$C_4$-alkynyl, $C_1$–$C_4$-alkoxy, $C_3$–$C_4$-alkenyloxy, $C_3$–$C_4$-alkynyloxy, each of which can be substituted by 1–6 halogen atoms, $NO_2$, cyano, halogen, thiocyanato, amino, or further a radical $C(=O)R^7$, $S(O)_nR^8$ or $NH—C(=O)R^9$;
$R^3$ is amino, halogen, thiocyanato, cyano, nitro, hydroxyl, $C_1$–$C_3$-alkyl, $C_1$–$C_3$-haloalkyl, or further a radical $S(O)_nR^8$, $N(R^{10})R^{11}$, $OR^{12}$, $SR^{13}$, $N=C(R^{14})—N(R^{15})R^{16}$ or, if $R^1$=hydrogen, additionally $N=C(R^{17})R^{18}$;
$R^4$ is halogen, a radical $XR^{19}$ or, if $R^3=N=C(R^{14})—N(R^{15})R^{16}$ and $N(R^{10})R^{11}$ with the meanings of $R^{10}$=hydrogen or $C(=O)R^7$ and $R^{11}=C_3$–$C_4$-alkenyl or $C_3$–$C_4$-alkynyl, or, if $R^6$=fluorine or trifluoromethyl, additionally hydrogen;

$R^5$ and $R^6$ independently of one another are halogen or $C_1$–$C_3$-haloalkyl;
$R^7$ is hydrogen, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy-$C_2$–$C_4$-alkyl, $C_3$–$C_6$-cycloalkyl, $C_1$–$C_4$-alkoxy, $C_1$–$C_4$-alkylamino or $C_1$–$C_4$-dialkylamino;
$R^8$ is $C_1$–$C_4$-alkyl, $C_1$–$C_4$-haloalkyl, $C_1$–$C_4$-alkoxy, chlorine, amino or $C_1$–$C_4$-alkylamino;
$R^9$ is $C_1$–$C_4$-alkyl, $C_1$–$C_4$-haloalkyl, $C_1$–$C_4$-alkoxy-$C_1$–$C_4$-alkyl, $C_2$–$C_4$-alkenyl, $C_2$–$C_4$-alkynyl or $C_1$–$C_4$-alkoxy;
$R^{10}$ is hydrogen, $C_1$–$C_4$-alkyl or a radical $C(=O)R^7$;
$R^{11}$ is hydrogen, $C_1$–$C_4$-alkyl, $C_3$–$C_4$-alkenyl, $C_3$–$C_4$-alkynyl, a radical $C(=O)R^7$ or $S(O)_nR^8$;
$R^{12}$ is $C_1$–$C_3$-alkoxy, $C_1$–$C_3$-haloalkoxy, $C_2$–$C_4$-alkenyloxy, $C_3$–$C_4$-alkynyloxy, $C_1$–$C_5$-alkoxycarbonyl-$C_1$–$C_4$-alkyl or $C_1$–$C_4$-alkoxy-$C_2$–$C_4$-alkoxycarbonyl-$C_1$–$C_6$-alkyl;
$R^{13}$ is $C_1$–$C_4$-alkoxycarbonyl-$C_1$–$C_4$-alkyl or $C_1$–$C_4$-alkoxy-$C_2$–$C_4$-alkoxycarbonyl-$C_1$–$C_6$-alkyl;
$R^{14}$ is hydrogen or $C_1$–$C_3$-alkyl;
$R^{15}$ is $C_1$–$C_4$-alkyl;
$R^{16}$ and $R^{17}$ independently of one another are hydrogen or $C_1$–$C_4$-alkyl;
$R^{18}$ is hydrogen, $C_1$–$C_4$-alkyl, $C_1$–$C_4$-haloalkyl, $C_1$–$C_3$-alkoxy-$C_1$–$C_3$-alkyl, $C_3$–$C_6$-cycloalkyl, $C_2$–$C_4$-alkenyl or $C_2$–$C_4$-alkynyl and
$R^{19}$ is hydrogen, $C_1$–$C_6$-alkyl, $C_2$–$C_6$-alkenyl or $C_2$–$C_6$-alkynyl, where these groups can carry up to 6 halogen atoms, $C_3$–$C_6$-cycloalkyl which for its part can carry up to three $C_1$–$C_3$-alkyl radicals or up to five halogen atoms, $C_1$–$C_6$-cyanoalkyl, $C_1$–$C_4$-alkoxy-$C_2$–$C_4$-alkyl, 3-oxetanyl, carboxyl-$C_1$–$C_6$-alkyl, $C_1$–$C_4$-alkoxycarbonyl-$C_1$–$C_6$-alkyl, $C_1$–$C_4$-alkoxy-$C_2$–$C_4$-alkoxycarbonyl-$C_1$–$C_6$-alkyl, $C_1$–$C_4$-alkylaminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-(α-alkylalkyliden)iminoxy-$C_2$–$C_6$-alkyl, cyclopropylmethyl, or, if X=O, additionally $C_1$–$C_4$-alkylamino, $C_1$–$C_4$-dialkylamino, $C_1$–$C_6$-alkylidenimino or α-($C_1$–$C_4$-alkyl)-$C_2$–$C_6$-alkylidenimino;
X is oxygen, sulfur, S=O or $SO_2$;
halogen is fluorine, chlorine, bromine or iodine and
n is 0, 1 or 2,
and the N-oxides and the agriculturally utilizable salts of the compounds I, have a good herbicidal action and are tolerable in gramineous crops such as wheat or rice.

The invention additionally relates to herbicidal compositions which contain the compounds I as active substances, and processes for the preparation of the compounds I and of herbicidal compositions using the compounds I.

The meanings mentioned above for the substituents $R^1$ to $R^{19}$ in the formula I are collective terms for an individual list of the separate group members. All carbon chains, ie. all alkyl, alkenyl, alkynyl, haloalkyl and haloalkoxy moieties, can be straight-chain or branched. Halogenated substituents preferably carry 1–6 identical or different halogen atoms.

Specific examples are:
halogen: fluorine, chlorine, bromine and iodine, preferably fluorine and chlorine;
$C_1$–$C_4$-alkyl: methyl, ethyl, n-propyl, 1-methylethyl, n-butyl, 1-methylpropyl, 2-methylpropyl and 1,1-dimethylethyl;
$C_1$–$C_6$-alkyl: $C_1$–$C_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_2$–$C_6$-alkenyl: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, preferably ethenyl and prop-2-en-1-yl;

$C_2$–$C_6$-alkynyl: ethynyl and $C_3$–$C_6$-alkynyl such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl, 1-methylprop-2-yn-1-yl;

$C_1$–$C_4$-haloalkyl: $C_1$–$C_4$-alkyl as mentioned above, which is partially or completely substituted by fluorine, chlorine and/or bromine, ie., for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl or 4-bromobutyl;

cyano-($C_1$–$C_6$)-alkyl: $C_1$–$C_6$-alkyl as mentioned above, where in each case a hydrogen atom is replaced by the cyano group, ie., for example, cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl, preferably cyanomethyl, 1-cyano-1-methylethyl;

$C_1$–$C_4$-alkoxy: methoxy, ethoxy, n-propoxy, 1-methylethoxy, n-butoxy, 1-methylpropoxy, 2-methylpropoxy or 1,1-dimethylethoxy;

$C_1$–$C_6$-alkoxy: $C_1$–$C_4$-alkoxy as mentioned above, and also n-pentoxy, 1-methylbutoxy, 2-methylbutoxy, 3-methylbutoxy, 1, 1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy:

$C_1$–$C_3$-haloalkoxy: $C_1$–$C_3$-alkoxy as mentioned above, which is partially or completely substituted by fluorine, chlorine, bromine and/or iodine, ie., for example, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy or 1-(bromomethyl)-2-bromoethoxy;

$C_2$–$C_4$-alkenyloxy: eth-1-en-1-yloxy, prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy;

$C_3$–$C_4$-alkynyloxy: prop-1-yn-1-yloxy, prop-2-yn-1-yloxy, n-but-1-yn-1-yloxy, n-but-1-yn-3-yloxy, n-but-1-yn-4-yloxy, n-but-2-yn-4-yloxy;

$C_3$–$C_6$-cycloalkyl: cyclopropyl, cyclobutyl, cyclopentyl or cyclohexyl;

$C_1$–$C_4$-alkylamino: methylamino, ethylamino, n-propylamino, 1-methylethylamino, n-butylamino, 1-methylpropylamino, 2-methylpropylamino and 1,1-dimethylethylamino, preferably methylamino and ethylamino;

di-($C_1$–$C_4$-alkyl)amino: N,N-dimethylamino, N,N-diethylamino, N,N-dipropylamino, N,N-di-(1- methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably dimethylamino and diethylamino;

$C_1$–$C_6$-alkylidenimino: ethylidenimino, propylidenimino, butylidenimino, 2-methylpropylidenimino, pentylidenimino, 2-methylbutylidenimino, 3-methylbutylidenimino, hexylidenimino, 2-methylpentylidenimino, 3-methylpentylidenimino or 2-ethylbutylidenimino.

With respect to the use of the compounds of the formula I according to the invention as herbicides, the variables preferably have the following meanings, in each case on their own or in combination:

$R^1$ is hydrogen;

$R^2$ is alkoxy, $C_1$–$C_4$-haloalkoxy, NO2, cyano, halogen, thiocyanato, amino, C(=O)$R^7$, S(O)$_n$$R^8$ or NH—C(=O)$R^9$;

$R^3$ is amino, halogen, thiocyanato, cyano, nitro, hydroxyl, $C_1$–$C_3$-alkyl, $C_1$–$C_3$-haloalkyl, further a radical S(O)$_n$$R^8$, N($R^{10}$)$R^{11}$, O$R^{12}$, S$R^{13}$, N=C($R^{14}$)—N($R^{15}$)$R^{16}$ or, if $R^1$=hydrogen, additionally N=C($R^{17}$)$R^{18}$;

$R^4$ is halogen, a radical X$R^{19}$ or, if $R^3$=N=C($R^{14}$)—N($R^{15}$)$R^{16}$ and N($R^{10}$)$R^{11}$ with the meanings of $R^{10}$=hydrogen or C(=O)$R^7$ and $R^{11}$=$C_3$–$C_4$-alkenyl or $C_3$–$C_4$-alkynyl, or, if $R^6$=fluorine or trifluoromethyl, additionally hydrogen;

$R^5$ and $R^6$ independently of one another are halogen or trifluoromethyl;

$R^7$ is $C_1$–$C_4$-alkyl, $C_1$–$C_4$-haloalkyl, $C_1$–$C_4$-alkoxy or $C_1$–$C_4$-alkylamino;

$R^8$ is $C_1$–$C_4$-alkyl, trifluoromethyl, $C_1$–$C_4$-alkoxy, chlorine, amino, methylamino or ethylamino;

$R^9$ is $C_1$–$C_4$-alkyl, $C_1$–$C_4$-haloalkyl or $C_1$–$C_4$-alkoxy;

$R^{10}$ is hydrogen, $C_1$–$C_4$-alkyl or C(=O)$R^7$;

$R^{11}$ is $C_1$–$C_4$-alkyl, $C_3$–$C_4$-alkenyl, $C_3$–$C_4$-alkynyl, C(=O)$R^7$ or S(O)$_n$$R^8$;

$R^{12}$ is $C_1$–$C_3$-alkoxy, $C_1$–$C_3$-haloalkoxy, $C_3$–$C_4$-alkenyl, $C_3$–$C_4$-alkynyl or $C_1$–$C_5$-alkoxycarbonyl-$C_1$–$C_4$-alkyl;

$R^{13}$ is $C_1$–$C_4$-alkoxycarbonyl-$C_1$–$C_4$-alkyl;

$R^{14}$, $R^{16}$ and $R^{17}$ are hydrogen or $C_1$–$C_3$-alkyl;

$R^{15}$ is $C_1$–$C_4$-alkyl;

$R^{18}$ is $C_1$–$C_4$-alkyl, $C_1$–$C_4$-haloalkyl or $C_2$–$C_4$-alkenyl and $R^{19}$ is $C_1$–$C_4$-alkyl, $C_3$–$C_4$-alkenyl, $C_3$–$C_4$-alkynyl, $C_1$–$C_4$-haloalkyl, $C_1$–$C_4$-cyanoalkyl, $C_1$–$C_4$-alkoxycarbonyl-$C_1$–$C_4$-alkyl, or, if X=O, additionally $C_1$–$C_4$-alkylamino or $C_1$–$C_4$-alkylidenimino;

X is oxygen or sulfur;

halogen is fluorine or chlorine and n is 0, 1 or 2.

Particularly preferred compounds are those shown in the following Tables 1–8:

TABLE 1

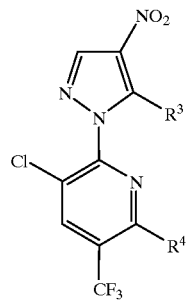

Ia

| No. | $R^3$ | $R^4$ | m.p. ° C., $^1$H-NMR [CDCl$_3$/TMS] δ |
|---|---|---|---|
| 1a.001 | NH$_2$ | F | 129–130 |
| 1a.002 | NH$_2$ | Cl | 125–128 |
| 1a.003 | NH—CH$_3$ | F | |
| 1a.004 | NH—CH$_3$ | Cl | |
| 1a.005 | NH—C$_2$H$_5$ | F | |
| 1a.006 | NH—C$_2$H$_5$ | Cl | |
| 1a.007 | NH-n-C$_3$H$_7$ | F | |
| 1a.008 | NH-n-C$_3$H$_7$ | Cl | |
| 1a.009 | NH—CH$_2$—CH=CH$_2$ | F | |
| 1a.010 | NH—CH$_2$—CH=CH$_2$ | Cl | |
| 1a.011 | NH—CH$_2$—C≡CH | F | |
| 1a.012 | NH—CH$_2$—C≡CH | Cl | |
| 1a.013 | N(CH$_3$)$_2$ | F | |
| 1a.014 | N(CH$_3$)$_2$ | Cl | |
| 1a.015 | N(CH$_3$)C$_2$H$_5$ | F | |
| 1a.016 | N(CH$_3$)C$_2$H$_5$ | Cl | |
| 1a.017 | N(C$_2$H$_5$)$_2$ | F | |
| 1a.018 | N(C$_2$H$_5$)$_2$ | Cl | |
| 1a.019 | Cl | F | |
| 1a.020 | Cl | Cl | |
| 1a.021 | Br | F | resin, pyraz. 8.44, s/1 pyrid. 8.39, d/1 |
| 1a.022 | Br | Cl | |
| 1a.023 | CN | F | |
| 1a.024 | CN | Cl | |
| 1a.025 | SCN | F | |
| 1a.026 | SCN | Cl | |
| 1a.027 | SO$_2$CH$_3$ | F | |
| 1a.028 | SO$_2$CH$_3$ | Cl | |
| 1a.029 | SO$_2$C$_2$H$_5$ | Cl | |
| 1a.030 | SOCH$_3$ | F | |
| 1a.031 | SOCH$_3$ | Cl | |
| 1a.032 | SCH$_3$ | F | |
| 1a.033 | SCH$_3$ | Cl | |
| 1a.034 | SO$_2$OCH$_3$ | F | |
| 1a.035 | SO$_2$OCH$_3$ | Cl | |
| 1a.036 | OH | F | |
| 1a.037 | OH | Cl | |
| 1a.038 | CH$_3$ | F | |
| 1a.039 | CH$_3$ | Cl | |
| 1a.040 | C$_2$H$_5$ | F | |
| 1a.041 | C$_2$H$_5$ | Cl | |
| 1a.042 | CF$_3$ | F | |
| 1a.043 | CF$_3$ | Cl | |
| 1a.044 | OCH$_3$ | F | |
| 1a.045 | OCH$_3$ | Cl | |
| 1a.046 | OC$_2$H$_5$ | F | |
| 1a.047 | OC$_2$H$_5$ | Cl | |
| 1a.048 | O-n-C$_3$H$_7$ | Cl | |
| 1a.049 | O—CHF$_2$ | F | |
| 1a.050 | O—CHF$_2$ | Cl | |
| 1a.051 | O—CF$_3$ | Cl | |

TABLE 1-continued

Ia

[Structure: pyrazole with NO2 group, connected via N to pyridine bearing Cl, CF3, and R4; R3 on pyrazole]

| No. | R³ | R⁴ | m.p. ° C., ¹H-NMR [CDCl₃/TMS] δ |
|---|---|---|---|
| 1a.052 | O—CH₂—CH=CH₂ | F | |
| 1a.053 | O—CH₂—CH=CH₂ | Cl | |
| 1a.054 | O—CH₂—C≡CH | F | |
| 1a.055 | O—CH₂—C≡CH | Cl | |
| 1a.056 | NH—C(=O)CH₃ | F | |
| 1a.057 | NH—C(=O)CH₃ | Cl | |
| 1a.058 | NH—C=(O)CH₂Cl | F | |
| 1a.059 | NH—C=(O)CH₂Cl | Cl | |
| 1a.060 | NH—C(=O)CF₃ | F | |
| 1a.061 | NH—C(=O)CF₃ | Cl | |
| 1a.062 | NHSO₂CH₃ | F | |
| 1a.063 | NHSO₂CH₃ | Cl | |
| 1a.064 | OCH₂—C(=O)OCH₃ | F | |
| 1a.065 | OCH₂—C(=O)OCH₃ | Cl | |
| 1a.066 | OCH₂—C(=O)OC₂H₅ | F | |
| 1a.067 | OCH₂—C(=O)OC₂H₅ | Cl | |
| 1a.068 | OCH₂C(=O)O-n-C₅H₁₁ | F | |
| 1a.069 | OCH₂C(=O)O-n-C₅H₁₁ | Cl | |
| 1a.070 | SCH₂C(=O)OCH₃ | F | |
| 1a.071 | SCH₂C(=O)OCH₃ | Cl | |
| 1a.072 | SCH₂C(=O)OC₂H₅ | F | |
| 1a.073 | SCH₂C(=O)OC₂H₅ | Cl | |
| 1a.074 | N=CH—N(CH₃)₂ | F | |
| 1a.075 | N=CH—N(CH₃)₂ | Cl | |
| 1a.076 | N=C(CH₃)—N(CH₃)₂ | F | |
| 1a.077 | N=C(CH₃)—N(CH₃)₂ | Cl | |
| 1a.078 | N=CH—CH₃ | F | |
| 1a.079 | N=CH—CH₃ | Cl | |
| 1a.080 | N=CH—C₂H₅ | F | |
| 1a.081 | N=CH—C₂H₅ | Cl | |
| 1a.082 | N=C(CH₃)—CH₃ | F | |
| 1a.083 | N=C(CH₃)—CH₃ | Cl | |
| 1a.084 | NO₂ | F | |
| 1a.085 | NO₂ | Cl | |
| 1a.086 | SO₂NH₂ | F | |
| 1a.087 | SO₂NH₂ | Cl | |
| 1a.088 | SO₂NHCH₃ | F | |
| 1a.089 | SO₂NHCH₃ | Cl | |
| 1a.090 | SO₂NHC₂H₅ | F | |
| 1a.091 | SO₂NHC₂H₅ | Cl | |

TABLE 2

IIa

[Structure: pyrazole with CN group, connected via N to pyridine bearing Cl, CF3, and R4; R3 on pyrazole]

| No. | R³ | R⁴ | m.p. ° C., ¹H-NMR [CDCl₃/TMS] δ |
|---|---|---|---|
| 2a.001 | NH₂ | F | 156–158 |
| 2a.002 | NH₂ | Cl | 168–171 |
| 2a.003 | NH—CH₃ | F | |
| 2a.004 | NH—CH₃ | Cl | |
| 2a.005 | NH—C₂H₅ | F | |
| 2a.006 | NH—C₂H₅ | Cl | |
| 2a.007 | NH-n-C₃H₇ | F | |
| 2a.008 | NH-n-C₃H₇ | Cl | |
| 2a.009 | NH—CH₂—CH=CH₂ | F | |
| 2a.010 | NH—CH₂—CH=CH₂ | Cl | |
| 2a.011 | NH—CH₂—C≡CH | F | |
| 2a.012 | NH—CH₂—C≡CH | Cl | |
| 2a.013 | N(CH₃)₂ | F | |
| 2a.014 | N(CH₃)₂ | Cl | |
| 2a.015 | N(CH₃)C₂H₅ | F | |
| 2a.016 | N(CH₃)C₂H₅ | Cl | |
| 2a.017 | N(C₂H₅)₂ | F | |
| 2a.018 | N(C₂H₅)₂ | Cl | |
| 2a.019 | Cl | F | |
| 2a.020 | Cl | Cl | |
| 2a.021 | Br | F | 104–108 |
| 2a.022 | Br | Cl | 121–122 |
| 2a.023 | CN | F | |
| 2a.024 | CN | Cl | |
| 2a.025 | SCN | F | |
| 2a.026 | SCN | Cl | |
| 2a.027 | SO₂CH₃ | F | |
| 2a.028 | SO₂CH₃ | Cl | |
| 2a.029 | SO₂C₂H₅ | Cl | |
| 2a.030 | SOCH₃ | F | |
| 2a.031 | SOCH₃ | Cl | |
| 2a.032 | SCH₃ | F | |
| 2a.033 | SCH₃ | Cl | |
| 2a.034 | SO₂OCH₃ | F | |
| 2a.035 | SO₂OCH₃ | Cl | |
| 2a.036 | OH | F | |
| 2a.037 | OH | Cl | |
| 2a.038 | CH₃ | F | |
| 2a.039 | CH₃ | Cl | |
| 2a.040 | C₂H₅ | F | |
| 2a.041 | C₂H₅ | Cl | |
| 2a.042 | CF₃ | F | |
| 2a.043 | CF₃ | Cl | |
| 2a.044 | OCH₃ | F | |
| 2a.045 | OCH₃ | Cl | |
| 2a.046 | OC₂H₅ | F | |
| 2a.047 | OC₂H₅ | Cl | |
| 2a.048 | O-n-C₃H₇ | Cl | |
| 2a.049 | O—CHF₂ | F | |
| 2a.050 | O—CHF₂ | Cl | |
| 2a.051 | O—CF₃ | Cl | |
| 2a.052 | O—CH₂—CH=CH₂ | F | |
| 2a.053 | O—CH₂—CH=CH₂ | Cl | |
| 2a.054 | O—CH₂—C≡CH | F | |
| 2a.055 | O—CH₂—C≡CH | Cl | |
| 2a.056 | NH—C(=O)CH₃ | F | |
| 2a.057 | NH—C(=O)CH₃ | Cl | |
| 2a.058 | NH—C=(O)CH₂Cl | F | |
| 2a.059 | NH—C=(O)CH₂Cl | Cl | |

TABLE 2-continued

IIa

Structure: Pyrazole with CN at position 4, R³ at position 5, N1 connected to pyridine bearing Cl, R⁴, and CF₃ substituents.

| No. | R³ | R⁴ | m.p. °C, $^1$H-NMR [CDCl$_3$/TMS] |
|---|---|---|---|
| 2a.060 | NH—C(=O)CF$_3$ | F | |
| 2a.061 | NH—C(=O)CF$_3$ | Cl | |
| 2a.062 | NHSO$_2$CH$_3$ | F | |
| 2a.063 | NHSO$_2$CH$_3$ | Cl | |
| 2a.064 | OCH$_2$—C(=O)OCH$_3$ | F | |
| 2a.065 | OCH$_2$—C(=O)OCH$_3$ | Cl | |
| 2a.066 | OCH$_2$—C(=O)OC$_2$H$_5$ | F | |
| 2a.067 | OCH$_2$—C(=O)OC$_2$H$_5$ | Cl | |
| 2a.068 | OCH$_2$C(=O)O-n-C$_5$H$_{11}$ | F | |
| 2a.069 | OCH$_2$C(=O)O-n-C$_5$H$_{11}$ | Cl | |
| 2a.070 | SCH$_2$C(=O)OCH$_3$ | F | |
| 2a.071 | SCH$_2$C(=O)OCH$_3$ | Cl | |
| 2a.072 | SCH$_2$C(=O)OC$_2$H$_5$ | F | |
| 2a.073 | SCH$_2$C(=O)OC$_2$H$_5$ | Cl | |
| 2a.074 | N=CH—N(CH$_3$)$_2$ | F | |
| 2a.075 | N=CH—N(CH$_3$)$_2$ | Cl | |
| 2a.076 | N=C(CH$_3$)—N(CH$_3$)$_2$ | F | |
| 2a.077 | N=C(CH$_3$)—N(CH$_3$)$_2$ | Cl | |
| 2a.078 | N=CH—CH$_3$ | F | |
| 2a.079 | N=CH—CH$_3$ | Cl | |
| 2a.080 | N=CH—C$_2$H$_5$ | F | |
| 2a.081 | N=CH—C$_2$H$_5$ | Cl | |
| 2a.082 | N=C(CH$_3$)—CH$_3$ | F | |
| 2a.083 | N=C(CH$_3$)—CH$_3$ | Cl | |
| 2a.084 | NO$_2$ | F | |
| 2a.085 | NO$_2$ | Cl | |
| 2a.086 | SO$_2$NH$_2$ | F | |
| 2a.087 | SO$_2$NH$_2$ | Cl | |
| 2a.088 | SO$_2$NHCH$_3$ | F | |
| 2a.089 | SO$_2$NHCH$_3$ | Cl | |
| 2a.090 | SO$_2$NHC$_2$H$_5$ | F | |
| 2a.091 | SO$_2$NHC$_2$H$_5$ | Cl | |

TABLE 3

IIIa

Structure: Pyrazole with Cl at position 4, R³ at position 5, N1 connected to pyridine bearing Cl, R⁴, and CF₃ substituents.

| No. | R³ | R⁴ | m.p. °C, $^1$H-NMR [CDCl$_3$/TMS] |
|---|---|---|---|
| 3a.001 | NH$_2$ | F | |
| 3a.002 | NH$_2$ | Cl | |
| 3a.003 | NH—CH$_3$ | F | |
| 3a.004 | NH—CH$_3$ | Cl | |
| 3a.005 | NH—C$_2$H$_5$ | F | |
| 3a.006 | NH—C$_2$H$_5$ | Cl | |
| 3a.007 | NH-n-C$_3$H$_7$ | F | |
| 3a.008 | NH-n-C$_3$H$_7$ | Cl | |
| 3a.009 | NH—CH$_2$—CH=CH$_2$ | F | |
| 3a.010 | NH—CH$_2$—CH=CH$_2$ | Cl | |
| 3a.011 | NH—CH$_2$—C≡CH | F | |
| 3a.012 | NH—CH$_2$—C≡CH | Cl | |
| 3a.013 | N(CH$_3$)$_2$ | F | |
| 3a.014 | N(CH$_3$)$_2$ | Cl | |
| 3a.015 | N(CH$_3$)C$_2$H$_5$ | F | |
| 3a.016 | N(CH$_3$)C$_2$H$_5$ | Cl | |
| 3a.017 | N(C$_2$H$_5$)$_2$ | F | |
| 3a.018 | N(C$_2$H$_5$)$_2$ | Cl | |
| 3a.019 | Cl | F | |
| 3a.020 | Cl | Cl | |
| 3a.021 | Br | F | |
| 3a.022 | Br | Cl | |
| 3a.023 | CN | F | |
| 3a.024 | CN | Cl | |
| 3a.025 | SCN | F | |
| 3a.026 | SCN | Cl | |
| 3a.027 | SO$_2$CH$_3$ | F | |
| 3a.028 | SO$_2$CH$_3$ | Cl | |
| 3a.029 | SO$_2$C$_2$H$_5$ | Cl | |
| 3a.030 | SOCH$_3$ | F | |
| 3a.031 | SOCH$_3$ | Cl | |
| 3a.032 | SCH$_3$ | F | |
| 3a.033 | SCH$_3$ | Cl | |
| 3a.034 | SO$_2$OCH$_3$ | F | |
| 3a.035 | SO$_2$OCH$_3$ | Cl | |
| 3a.036 | OH | F | |
| 3a.037 | OH | Cl | |
| 3a.038 | CH$_3$ | F | |
| 3a.039 | CH$_3$ | Cl | |
| 3a.040 | C$_2$H$_5$ | F | |
| 3a.041 | C$_2$H$_5$ | Cl | |
| 3a.042 | CF$_3$ | F | |
| 3a.043 | CF$_3$ | Cl | |
| 3a.044 | OCH$_3$ | F | |
| 3a.045 | OCH$_3$ | Cl | |
| 3a.046 | OC$_2$H$_5$ | F | |
| 3a.047 | OC$_2$H$_5$ | Cl | |
| 3a.048 | O-n-C$_3$H$_7$ | Cl | |
| 3a.049 | O—CHF$_2$ | F | |
| 3a.050 | O—CHF$_2$ | Cl | |
| 3a.051 | O—CF$_3$ | Cl | |
| 3a.052 | O—CH$_2$—CH=CH$_2$ | F | |
| 3a.053 | O—CH$_2$—CH=CH$_2$ | Cl | |
| 3a.054 | O—CH$_2$—C≡CH | F | |
| 3a.055 | O—CH$_2$—C≡CH | Cl | |
| 3a.056 | NH—C(=O)CH$_3$ | F | |
| 3a.057 | NH—C(=O)CH$_3$ | Cl | |
| 3a.058 | NH—C=(O)CH$_2$Cl | F | |
| 3a.059 | NH—C=(O)CH$_2$Cl | Cl | |
| 3a.060 | NH—C(=O)CF$_3$ | F | |
| 3a.061 | NH—C(=O)CF$_3$ | Cl | |

TABLE 3-continued

IIIa

| No. | R³ | R⁴ | m.p. ° C., ¹H-NMR [CDCl₃/TMS] |
|---|---|---|---|
| 3a.062 | NHSO₂CH₃ | F | |
| 3a.063 | NHSO₂CH₃ | Cl | |
| 3a.064 | OCH₂—C(=O)OCH₃ | F | |
| 3a.065 | OCH₂—C(=O)OCH₃ | Cl | |
| 3a.066 | OCH₂—C(=O)OC₂H₅ | F | |
| 3a.067 | OCH₂—C(=O)OC₂H₅ | Cl | |
| 3a.068 | OCH₂C(=O)O-n-C₅H₁₁ | F | |
| 3a.069 | OCH₂C(=O)O-n-C₅H₁₁ | Cl | |
| 3a.070 | SCH₂C(=O)OCH₃ | F | |
| 3a.071 | SCH₂C(=O)OCH₃ | Cl | |
| 3a.072 | SCH₂C(=O)OC₂H₅ | F | |
| 3a.073 | SCH₂C(=O)OC₂H₅ | Cl | |
| 3a.074 | N=CH—N(CH₃)₂ | F | |
| 3a.075 | N=CH—N(CH₃)₂ | Cl | |
| 3a.076 | N=C(CH₃)—N(CH₃)₂ | F | |
| 3a.077 | N=C(CH₃)—N(CH₃)₂ | Cl | |
| 3a.078 | N=CH—CH₃ | F | |
| 3a.079 | N=CH—CH₃ | Cl | |
| 3a.080 | N=CH—C₂H₅ | F | |
| 3a.081 | N=CH—C₂H₅ | Cl | |
| 3a.082 | N=C(CH₃)—CH₃ | F | |
| 3a.083 | N=C(CH₃)—CH₃ | Cl | |
| 3a.084 | NO₂ | F | |
| 3a.085 | NO₂ | Cl | |
| 3a.086 | SO₂NH₂ | F | |
| 3a.087 | SO₂NH₂ | Cl | |
| 3a.088 | SO₂NHCH₃ | F | |
| 3a.089 | SO₂NHCH₃ | Cl | |
| 3a.090 | SO₂NHC₂H₅ | F | |
| 3a.091 | SO₂NHC₂H₅ | Cl | |

TABLE 4

IVa

| No. | R³ | R⁴ | m.p. ° C., ¹H-NMR [CDCl₃/TMS] |
|---|---|---|---|
| 4a.001 | NH₂ | F | |
| 4a.002 | NH₂ | Cl | |
| 4a.003 | NH—CH₃ | F | |
| 4a.004 | NH—CH₃ | Cl | |
| 4a.005 | NH—C₂H₅ | F | |
| 4a.006 | NH—C₂H₅ | Cl | |
| 4a.007 | NH-n-C₃H₇ | F | |
| 4a.008 | NH-n-C₃H₇ | Cl | |
| 4a.009 | NH—CH₂—CH=CH₂ | F | |
| 4a.010 | NH—CH₂—CH=CH₂ | Cl | |
| 4a.011 | NH—CH₂—C≡CH | F | |
| 4a.012 | NH—CH₂—C≡CH | Cl | |
| 4a.013 | N(CH₃)₂ | F | |
| 4a.014 | N(CH₃)₂ | Cl | |
| 4a.015 | N(CH₃)C₂H₅ | F | |
| 4a.016 | N(CH₃)C₂H₅ | Cl | |
| 4a.017 | N(C₂H₅)₂ | F | |
| 4a.018 | N(C₂H₅)₂ | Cl | |
| 4a.019 | Cl | F | |
| 4a.020 | Cl | Cl | |
| 4a.021 | Br | F | |
| 4a.022 | Br | Cl | |
| 4a.023 | CN | F | |
| 4a.024 | CN | Cl | |
| 4a.025 | SCN | F | |
| 4a.026 | SCN | Cl | |
| 4a.027 | SO₂CH₃ | F | |
| 4a.028 | SO₂CH₃ | Cl | |
| 4a.029 | SO₂C₂H₅ | Cl | |
| 4a.030 | SOCH₃ | F | |
| 4a.031 | SOCH₃ | Cl | |
| 4a.032 | SCH₃ | F | |
| 4a.033 | SCH₃ | Cl | |
| 4a.034 | SO₂OCH₃ | F | |
| 4a.035 | SO₂OCH₃ | Cl | |
| 4a.036 | OH | F | |
| 4a.037 | OH | Cl | |
| 4a.038 | CH₃ | F | |
| 4a.039 | CH₃ | Cl | |
| 4a.040 | C₂H₅ | F | |
| 4a.041 | C₂H₅ | Cl | |
| 4a.042 | CF₃ | F | |
| 4a.043 | CF₃ | Cl | |
| 4a.044 | OCH₃ | F | |
| 4a.045 | OCH₃ | Cl | |
| 4a.046 | OC₂H₅ | F | |
| 4a.047 | OC₂H₅ | Cl | |
| 4a.048 | O-n-C₃H₇ | Cl | |
| 4a.049 | O—CHF₂ | F | |
| 4a.050 | O—CHF₂ | Cl | |
| 4a.051 | O—CF₃ | Cl | |
| 4a.052 | O—CH₂—CH=CH₂ | F | |
| 4a.053 | O—CH₂—CH=CH₂ | Cl | |
| 4a.054 | O—CH₂—C≡CH | F | |
| 4a.055 | O—CH₂—C≡CH | Cl | |
| 4a.056 | NH—C(=O)CH₃ | F | |
| 4a.057 | NH—C(=O)CH₃ | Cl | |
| 4a.058 | NH—C=(O)CH₂Cl | F | |
| 4a.059 | NH—C=(O)CH₂Cl | Cl | |
| 4a.060 | NH—C(=O)CF₃ | F | |
| 4a.061 | NH—C(=O)CF₃ | Cl | |
| 4a.062 | NHSO₂CH₃ | F | |
| 4a.063 | NHSO₂CH₃ | Cl | |

TABLE 4-continued

IVa

| No. | R³ | R⁴ | m.p. ° C., ¹H-NMR [CDCl₃/TMS] |
|---|---|---|---|
| 4a.064 | OCH₂—C(=O)OCH₃ | F | |
| 4a.065 | OCH₂—C(=O)OCH₃ | Cl | |
| 4a.066 | OCH₂—C(=O)OC₂H₅ | F | |
| 4a.067 | OCH₂—C(=O)OC₂H₅ | Cl | |
| 4a.068 | OCH₂C(=O)O-n-C₅H₁₁ | F | |
| 4a.069 | OCH₂C(=O)O-n-C₅H₁₁ | Cl | |
| 4a.070 | SCH₂C(=O)OCH₃ | F | |
| 4a.071 | SCH₂C(=O)OCH₃ | Cl | |
| 4a.072 | SCH₂C(=O)OC₂H₅ | F | |
| 4a.073 | SCH₂C(=O)OC₂H₅ | Cl | |
| 4a.074 | N=CH—N(CH₃)₂ | F | |
| 4a.075 | N=CH—N(CH₃)₂ | Cl | |
| 4a.076 | N=C(CH₃)—N(CH₃)₂ | F | |
| 4a.077 | N=C(CH₃)—N(CH₃)₂ | Cl | |
| 4a.078 | N=CH—CH₃ | F | |
| 4a.079 | N=CH—CH₃ | Cl | |
| 4a.080 | N=CH—C₂H₅ | F | |
| 4a.081 | N=CH—C₂H₅ | Cl | |
| 4a.082 | N=C(CH₃)—CH₃ | F | |
| 4a.083 | N=C(CH₃)—CH₃ | Cl | |
| 4a.084 | NO₂ | F | |
| 4a.085 | NO₂ | Cl | |
| 4a.086 | SO₂NH₂ | F | |
| 4a.087 | SO₂NH₂ | Cl | |
| 4a.088 | SO₂NHCH₃ | F | |
| 4a.089 | SO₂NHCH₃ | Cl | |
| 4a.090 | SO₂NHC₂H₅ | F | |
| 4a.091 | SO₂NHC₂H₅ | Cl | |

TABLE 5

Va

| No. | R³ | R⁴ | m.p. ° C., ¹H-NMR [CDCl₃/TMS] |
|---|---|---|---|
| 5a.001 | NH₂ | F | |
| 5a.002 | NH₂ | Cl | |
| 5a.003 | NH—CH₃ | F | |
| 5a.004 | NH—CH₃ | Cl | |
| 5a.005 | NH—C₂H₅ | F | |
| 5a.006 | NH—C₂H₅ | Cl | |

TABLE 5-continued

Va

| No. | R³ | R⁴ | m.p. ° C., ¹H-NMR [CDCl₃/TMS] |
|---|---|---|---|
| 5a.007 | NH-n-C₃H₇ | F | |
| 5a.008 | NH-n-C₃H₇ | Cl | |
| 5a.009 | NH—CH₂—CH=CH₂ | F | |
| 5a.010 | NH—CH₂—CH=CH₂ | Cl | |
| 5a.011 | NH—CH₂—C≡CH | F | |
| 5a.012 | NH—CH₂—C≡CH | Cl | |
| 5a.013 | N(CH₃)₂ | F | |
| 5a.014 | N(CH₃)₂ | Cl | |
| 5a.015 | N(CH₃)C₂H₅ | F | |
| 5a.016 | N(CH₃)C₂H₅ | Cl | |
| 5a.017 | N(C₂H₅)₂ | F | |
| 5a.018 | N(C₂H₅)₂ | Cl | |
| 5a.019 | Cl | F | |
| 5a.020 | Cl | Cl | |
| 5a.021 | Br | F | |
| 5a.022 | Br | Cl | |
| 5a.023 | CN | F | |
| 5a.024 | CN | Cl | |
| 5a.025 | SCN | F | |
| 5a.026 | SCN | Cl | |
| 5a.027 | SO₂CH₃ | F | |
| 5a.028 | SO₂CH₃ | Cl | |
| 5a.029 | SO₂C₂H₅ | Cl | |
| 5a.030 | SOCH₃ | F | |
| 5a.031 | SOCH₃ | Cl | |
| 5a.032 | SCH₃ | F | |
| 5a.033 | SCH₃ | Cl | |
| 5a.034 | SO₂OCH₃ | F | |
| 5a.035 | SO₂OCH₃ | Cl | |
| 5a.036 | OH | F | |
| 5a.037 | OH | Cl | |
| 5a.038 | CH₃ | F | |
| 5a.039 | CH₃ | Cl | |
| 5a.040 | C₂H₅ | F | |
| 5a.041 | C₂H₅ | Cl | |
| 5a.042 | CF₃ | F | |
| 5a.043 | CF₃ | Cl | |
| 5a.044 | OCH₃ | F | |
| 5a.045 | OCH₃ | Cl | |
| 5a.046 | OC₂H₅ | F | |
| 5a.047 | OC₂H₅ | Cl | |
| 5a.048 | O-n-C₃H₇ | Cl | |
| 5a.049 | O—CHF₂ | F | |
| 5a.050 | O—CHF₂ | Cl | |
| 5a.051 | O—CF₃ | Cl | |
| 5a.052 | O—CH₂—CH=CH₂ | F | |
| 5a.053 | O—CH₂—CH=CH₂ | Cl | |
| 5a.054 | O—CH₂—C≡CH | F | |
| 5a.055 | O—CH₂—C≡CH | Cl | |
| 5a.056 | NH—C(=O)CH₃ | F | |
| 5a.057 | NH—C(=O)CH₃ | Cl | |
| 5a.058 | NH—C=(O)CH₂Cl | F | |
| 5a.059 | NH—C=(O)CH₂Cl | Cl | |
| 5a.060 | NH—C(=O)CF₃ | F | |
| 5a.061 | NH—C(=O)CF₃ | Cl | |
| 5a.062 | NHSO₂CH₃ | F | |
| 5a.063 | NHSO₂CH₃ | Cl | |
| 5a.064 | OCH₂—C(=O)OCH₃ | F | |
| 5a.065 | OCH₂—C(=O)OCH₃ | Cl | |

TABLE 5-continued

Va (Structure: pyrazole with SO₂CH₃ at position 4, R³ at position 5, N-linked to pyridine bearing Cl, R⁴, and CF₃)

| No. | R³ | R⁴ | m.p. °C., ¹H-NMR [CDCl₃/TMS] |
|---|---|---|---|
| 5a.066 | OCH₂—C(=O)OC₂H₅ | F | |
| 5a.067 | OCH₂—C(=O)OC₂H₅ | Cl | |
| 5a.068 | OCH₂C(=O)O-n-C₅H₁₁ | F | |
| 5a.069 | OCH₂C(=O)O-n-C₅H₁₁ | Cl | |
| 5a.070 | SCH₂C(=O)OCH₃ | F | |
| 5a.071 | SCH₂C(=O)OCH₃ | Cl | |
| 5a.072 | SCH₂C(=O)OC₂H₅ | F | |
| 5a.073 | SCH₂C(=O)OC₂H₅ | Cl | |
| 5a.074 | N=CH—N(CH₃)₂ | F | |
| 5a.075 | N=CH—N(CH₃)₂ | Cl | |
| 5a.076 | N=C(CH₃)—N(CH₃)₂ | F | |
| 5a.077 | N=C(CH₃)—N(CH₃)₂ | Cl | |
| 5a.078 | N=CH—CH₃ | F | |
| 5a.079 | N=CH—CH₃ | Cl | |
| 5a.080 | N=CH—C₂H₅ | F | |
| 5a.081 | N=CH—C₂H₅ | Cl | |
| 5a.082 | N=C(CH₃)—CH₃ | F | |
| 5a.083 | N=C(CH₃)—CH₃ | Cl | |
| 5a.084 | NO₂ | F | |
| 5a.085 | NO₂ | Cl | |
| 5a.086 | SO₂NH₂ | F | |
| 5a.087 | SO₂NH₂ | Cl | |
| 5a.088 | SO₂NHCH₃ | F | |
| 5a.089 | SO₂NHCH₃ | Cl | |
| 5a.090 | SO₂NHC₂H₅ | F | |
| 5a.091 | SO₂NHC₂H₅ | Cl | |

TABLE 6

VIa (Structure: pyrazole with SCN at position 4, R³ at position 5, N-linked to pyridine bearing Cl, R⁴, and CF₃)

| No. | R³ | R⁴ | m.p. °C., ¹H-NMR [CDCl₃/TMS] |
|---|---|---|---|
| 6a.001 | NH₂ | F | 109–114 |
| 6a.002 | NH₂ | Cl | |
| 6a.003 | NH—CH₃ | F | |
| 6a.004 | NH—CH₃ | Cl | |
| 6a.005 | NH—C₂H₅ | F | |
| 6a.006 | NH—C₂H₅ | Cl | |
| 6a.007 | NH-n-C₃H₇ | F | |
| 6a.008 | NH-n-C₃H₇ | Cl | |

TABLE 6-continued

VIa (Structure: pyrazole with SCN at position 4, R³ at position 5, N-linked to pyridine bearing Cl, R⁴, and CF₃)

| No. | R³ | R⁴ | m.p. °C., ¹H-NMR [CDCl₃/TMS] |
|---|---|---|---|
| 6a.009 | NH—CH₂—CH=CH₂ | F | |
| 6a.010 | NH—CH₂—CH=CH₂ | Cl | |
| 6a.011 | NH—CH₂—C≡CH | F | |
| 6a.012 | NH—CH₂—C≡CH | Cl | |
| 6a.013 | N(CH₃)₂ | F | |
| 6a.014 | N(CH₃)₂ | Cl | |
| 6a.015 | N(CH₃)C₂H₅ | F | |
| 6a.016 | N(CH₃)C₂H₅ | Cl | |
| 6a.017 | N(C₂H₅)₂ | F | |
| 6a.018 | N(C₂H₅)₂ | Cl | |
| 6a.019 | Cl | F | |
| 6a.020 | Cl | Cl | |
| 6a.021 | Br | F | |
| 6a.022 | Br | Cl | |
| 6a.023 | CN | F | |
| 6a.024 | CN | Cl | |
| 6a.025 | SCN | F | |
| 6a.026 | SCN | Cl | |
| 6a.027 | SO₂CH₃ | F | |
| 6a.028 | SO₂CH₃ | Cl | |
| 6a.029 | SO₂C₂H₅ | Cl | |
| 6a.030 | SOCH₃ | F | |
| 6a.031 | SOCH₃ | Cl | |
| 6a.032 | SCH₃ | F | |
| 6a.033 | SCH₃ | Cl | |
| 6a.034 | SO₂OCH₃ | F | |
| 6a.035 | SO₂OCH₃ | Cl | |
| 6a.036 | OH | F | |
| 6a.037 | OH | Cl | |
| 6a.038 | CH₃ | F | |
| 6a.039 | CH₃ | Cl | |
| 6a.040 | C₂H₅ | F | |
| 6a.041 | C₂H₅ | Cl | |
| 6a.042 | CF₃ | F | |
| 6a.043 | CF₃ | Cl | |
| 6a.044 | OCH₃ | F | |
| 6a.045 | OCH₃ | Cl | |
| 6a.046 | OC₂H₅ | F | |
| 6a.047 | OC₂H₅ | Cl | |
| 6a.048 | O-n-C₃H₇ | Cl | |
| 6a.049 | O—CHF₂ | F | |
| 6a.050 | O—CHF₂ | Cl | |
| 6a.051 | O—CF₃ | Cl | |
| 6a.052 | O—CH₂—CH=CH₂ | F | |
| 6a.053 | O—CH₂—CH=CH₂ | Cl | |
| 6a.054 | O—CH₂—C≡CH | F | |
| 6a.055 | O—CH₂—C≡CH | Cl | |
| 6a.056 | NH—C(=O)CH₃ | F | |
| 6a.057 | NH—C(=O)CH₃ | Cl | |
| 6a.058 | NH—C=(O)CH₂Cl | F | |
| 6a.059 | NH—C=(O)CH₂Cl | Cl | |
| 6a.060 | NH—C(=O)CF₃ | F | |
| 6a.061 | NH—C(=O)CF₃ | Cl | |
| 6a.062 | NHSO₂CH₃ | F | |
| 6a.063 | NHSO₂CH₃ | Cl | |
| 6a.064 | OCH₂—C(=O)OCH₃ | F | |
| 6a.065 | OCH₂—C(=O)OCH₃ | Cl | |
| 6a.066 | OCH₂—C(=O)OC₂H₅ | F | |
| 6a.067 | OCH₂—C(=O)OC₂H₅ | Cl | |

TABLE 6-continued

VIa

| No. | R³ | R⁴ | m.p. ° C., ¹H-NMR [CDCl₃/TMS] |
|---|---|---|---|
| 6a.068 | OCH₂C(=O)O-n-C₅H₁₁ | F | |
| 6a.069 | OCH₂C(=O)O-n-C₅H₁₁ | Cl | |
| 6a.070 | SCH₂C(=O)OCH₃ | F | |
| 6a.071 | SCH₂C(=O)OCH₃ | Cl | |
| 6a.072 | SCH₂C(=O)OC₂H₅ | F | |
| 6a.073 | SCH₂C(=O)OC₂H₅ | Cl | |
| 6a.074 | N=CH—N(CH₃)₂ | F | |
| 6a.075 | N=CH—N(CH₃)₂ | Cl | |
| 6a.076 | N=C(CH₃)—N(CH₃)₂ | F | |
| 6a.077 | N=C(CH₃)—N(CH₃)₂ | Cl | |
| 6a.078 | N=CH—CH₃ | F | |
| 6a.079 | N=CH—CH₃ | Cl | |
| 6a.080 | N=CH—C₂H₅ | F | |
| 6a.081 | N=CH—C₂H₅ | Cl | |
| 6a.082 | N=C(CH₃)—CH₃ | F | |
| 6a.083 | N=C(CH₃)—CH₃ | Cl | |
| 6a.084 | NO₂ | F | |
| 6a.085 | NO₂ | Cl | |
| 6a.086 | SO₂NH₂ | F | |
| 6a.087 | SO₂NH₂ | Cl | |
| 6a.088 | SO₂NHCH₃ | F | |
| 6a.089 | SO₂NHCH₃ | Cl | |
| 6a.090 | SO₂NHC₂H₅ | F | |
| 6a.091 | SO₂NHC₂H₅ | Cl | |

TABLE 7

VIIa

| No. | R³ | R⁴ | m.p. ° C., ¹H-NMR [CDCl₃/TMS] |
|---|---|---|---|
| 7a.001 | NH₂ | F | |
| 7a.002 | NH₂ | Cl | |
| 7a.003 | NH—CH₃ | F | |
| 7a.004 | NH—CH₃ | Cl | |
| 7a.005 | NH—C₂H₅ | F | |
| 7a.006 | NH—C₂H₅ | Cl | |
| 7a.007 | NH-n-C₃H₇ | F | |
| 7a.008 | NH-n-C₃H₇ | Cl | |
| 7a.009 | NH—CH₂—CH=CH₂ | F | |
| 7a.010 | NH—CH₂—CH=CH₂ | Cl | |

TABLE 7-continued

VIIa

| No. | R³ | R⁴ | m.p. ° C., ¹H-NMR [CDCl₃/TMS] |
|---|---|---|---|
| 7a.011 | NH—CH₂—C≡CH | F | |
| 7a.012 | NH—CH₂—C≡CH | Cl | |
| 7a.013 | N(CH₃)₂ | F | |
| 7a.014 | N(CH₃)₂ | Cl | |
| 7a.015 | N(CH₃)C₂H₅ | F | |
| 7a.016 | N(CH₃)C₂H₅ | Cl | |
| 7a.017 | N(C₂H₅)₂ | F | |
| 7a.018 | N(C₂H₅)₂ | Cl | |
| 7a.019 | Cl | F | |
| 7a.020 | Cl | Cl | |
| 7a.021 | Br | F | |
| 7a.022 | Br | Cl | |
| 7a.023 | CN | F | |
| 7a.024 | CN | Cl | |
| 7a.025 | SCN | F | |
| 7a.026 | SCN | Cl | |
| 7a.027 | SO₂CH₃ | F | |
| 7a.028 | SO₂CH₃ | Cl | |
| 7a.029 | SO₂C₂H₅ | Cl | |
| 7a.030 | SOCH₃ | F | |
| 7a.031 | SOCH₃ | Cl | |
| 7a.032 | SCH₃ | F | |
| 7a.033 | SCH₃ | Cl | |
| 7a.034 | SO₂OCH₃ | F | |
| 7a.035 | SO₂OCH₃ | Cl | |
| 7a.036 | OH | F | |
| 7a.037 | OH | Cl | |
| 7a.038 | CH₃ | F | |
| 7a.039 | CH₃ | Cl | |
| 7a.040 | C₂H₅ | F | |
| 7a.041 | C₂H₅ | Cl | |
| 7a.042 | CF₃ | F | |
| 7a.043 | CF₃ | Cl | |
| 7a.044 | OCH₃ | F | |
| 7a.045 | OCH₃ | Cl | |
| 7a.046 | OC₂H₅ | F | |
| 7a.047 | OC₂H₅ | Cl | |
| 7a.048 | O-n-C₃H₇ | Cl | |
| 7a.049 | O—CHF₂ | F | |
| 7a.050 | O—CHF₂ | Cl | |
| 7a.051 | O—CF₃ | Cl | |
| 7a.052 | O—CH₂—CH=CH₂ | F | |
| 7a.053 | O—CH₂—CH=CH₂ | Cl | |
| 7a.054 | O—CH₂—C≡CH | F | |
| 7a.055 | O—CH₂—C≡CH | Cl | |
| 7a.056 | NH—C(=O)CH₃ | F | |
| 7a.057 | NH—C(=O)CH₃ | Cl | |
| 7a.058 | NH—C=(O)CH₂Cl | F | |
| 7a.059 | NH—C=(O)CH₂Cl | Cl | |
| 7a.060 | NH—C(=O)CF₃ | F | |
| 7a.061 | NH—C(=O)CF₃ | Cl | |
| 7a.062 | NHSO₂CH₃ | F | |
| 7a.063 | NHSO₂CH₃ | Cl | |
| 7a.064 | OCH₂—C(=O)OCH₃ | F | |
| 7a.065 | OCH₂—C(=O)OCH₃ | Cl | |
| 7a.066 | OCH₂—C(=O)OC₂H₅ | F | |
| 7a.067 | OCH₂—C(=O)OC₂H₅ | Cl | |
| 7a.068 | OCH₂C(=O)O-n-C₅H₁₁ | F | |
| 7a.069 | OCH₂C(=O)O-n-C₅H₁₁ | Cl | |

TABLE 7-continued

VIIa

| No. | R³ | R⁴ | m.p. ° C., ¹H-NMR [CDCl₃/TMS] |
|---|---|---|---|
| 7a.070 | SCH₂C(=O)OCH₃ | F | |
| 7a.071 | SCH₂C(=O)OCH₃ | Cl | |
| 7a.072 | SCH₂C(=O)OC₂H₅ | F | |
| 7a.073 | SCH₂C(=O)OC₂H₅ | Cl | |
| 7a.074 | N=CH—N(CH₃)₂ | F | |
| 7a.075 | N=CH—N(CH₃)₂ | Cl | |
| 7a.076 | N=C(CH₃)—N(CH₃)₂ | F | |
| 7a.077 | N=C(CH₃)—N(CH₃)₂ | Cl | |
| 7a.078 | N=CH—CH₃ | F | |
| 7a.079 | N=CH—CH₃ | Cl | |
| 7a.080 | N=CH—C₂H₅ | F | |
| 7a.081 | N=CH—C₂H₅ | Cl | |
| 7a.082 | N=C(CH₃)—CH₃ | F | |
| 7a.083 | N=C(CH₃)—CH₃ | Cl | |
| 7a.084 | NO₂ | F | |
| 7a.085 | NO₂ | Cl | |
| 7a.086 | SO₂NH₂ | F | |
| 7a.087 | SO₂NH₂ | Cl | |
| 7a.088 | SO₂NHCH₃ | F | |
| 7a.089 | SO₂NHCH₃ | Cl | |
| 7a.090 | SO₂NHC₂H₅ | F | |
| 7a.091 | SO₂NHC₂H₅ | Cl | |

TABLE 8

VIIIa

| No. | R³ | R⁴ | m.p. ° C., ¹H-NMR [CDCl₃/TMS] |
|---|---|---|---|
| 8a.001 | NH₂ | F | 90–95 |
| 8a.002 | NH₂ | Cl | 143–144 |
| 8a.003 | NH—CH₃ | F | |
| 8a.004 | NH—CH₃ | Cl | |
| 8a.005 | NH—C₂H₅ | F | |
| 8a.006 | NH—C₂H₅ | Cl | |
| 8a.007 | NH-n-C₃H₇ | F | |
| 8a.008 | NH-n-C₃H₇ | Cl | |
| 8a.009 | NH—CH₂—CH=CH₂ | F | |
| 8a.010 | NH—CH₂—CH=CH₂ | Cl | |
| 8a.011 | NH—CH₂—C≡CH | F | |
| 8a.012 | NH—CH₂—C≡CH | Cl | |

TABLE 8-continued

VIIIa

| No. | R³ | R⁴ | m.p. ° C., ¹H-NMR [CDCl₃/TMS] |
|---|---|---|---|
| 8a.013 | N(CH₃)₂ | F | |
| 8a.014 | N(CH₃)₂ | Cl | |
| 8a.015 | N(CH₃)C₂H₅ | F | |
| 8a.016 | N(CH₃)C₂H₅ | Cl | |
| 8a.017 | N(C₂H₅)₂ | F | |
| 8a.018 | N(C₂H₅)₂ | Cl | |
| 8a.019 | Cl | F | |
| 8a.020 | Cl | Cl | |
| 8a.021 | Br | F | 89–90 |
| 8a.022 | Br | Cl | |
| 8a.023 | CN | F | |
| 8a.024 | CN | Cl | |
| 8a.025 | SCN | F | |
| 8a.026 | SCN | Cl | |
| 8a.027 | SO₂CH₃ | F | |
| 8a.028 | SO₂CH₃ | Cl | |
| 8a.029 | SO₂C₂H₅ | F | |
| 8a.030 | SOCH₃ | F | |
| 8a.031 | SOCH₃ | Cl | |
| 8a.032 | SCH₃ | F | |
| 8a.033 | SCH₃ | Cl | |
| 8a.034 | SO₂OCH₃ | F | |
| 8a.035 | SO₂OCH₃ | Cl | |
| 8a.036 | OH | F | |
| 8a.037 | OH | Cl | |
| 8a.038 | CH₃ | F | |
| 8a.039 | CH₃ | Cl | |
| 8a.040 | C₂H₅ | F | |
| 8a.041 | C₂H₅ | Cl | |
| 8a.042 | CF₃ | F | |
| 8a.043 | CF₃ | Cl | |
| 8a.044 | OCH₃ | F | |
| 8a.045 | OCH₃ | Cl | |
| 8a.046 | OC₂H₅ | F | |
| 8a.047 | OC₂H₅ | Cl | |
| 8a.048 | O-n-C₃H₇ | Cl | |
| 8a.049 | O—CHF₂ | F | |
| 8a.050 | O—CHF₂ | Cl | |
| 8a.051 | O—CF₃ | Cl | |
| 8a.052 | O—CH₂—CH=CH₂ | F | |
| 8a.053 | O—CH₂—CH=CH₂ | Cl | |
| 8a.054 | O—CH₂—C≡CH | F | |
| 8a.055 | O—CH₂—C≡CH | Cl | |
| 8a.056 | NH—C(=O)CH₃ | F | |
| 8a.057 | NH—C(=O)CH₃ | Cl | |
| 8a.058 | NH—C=(O)CH₂Cl | F | |
| 8a.059 | NH—C(=O)CH₂Cl | Cl | |
| 8a.060 | NH—C(=O)CF₃ | F | |
| 8a.061 | NH—C(=O)CF₃ | Cl | |
| 8a.062 | NHSO₂CH₃ | F | |
| 8a.063 | NHSO₂CH₃ | Cl | |
| 8a.064 | OCH₂—C(=O)OCH₃ | F | |
| 8a.065 | OCH₂—C(=O)OCH₃ | Cl | |
| 8a.066 | OCH₂—C(=O)OC₂H₅ | F | |
| 8a.067 | OCH₂—C(=O)OC₂H₅ | Cl | |
| 8a.068 | OCH₂C(=O)O-n-C₅H₁₁ | F | |
| 8a.069 | OCH₂C(=O)O-n-C₅H₁₁ | Cl | |
| 8a.070 | SCH₂C(=O)OCH₃ | F | |
| 8a.071 | SCH₂C(=O)OCH₃ | Cl | |

TABLE 8-continued

VIIIa

![VIIIa structure]

| No. | R³ | R⁴ | m.p. °C., ¹H-NMR [CDCl₃/TMS] |
|---|---|---|---|
| 8a.072 | SCH₂C(=O)OC₂H₅ | F | |
| 8a.073 | SCH₂C(=O)OC₂H₅ | Cl | |
| 8a.074 | N=CH—N(CH₃)₂ | F | |
| 8a.075 | N=CH—N(CH₃)₂ | Cl | |
| 8a.076 | N=C(CH₃)—N(CH₃)₂ | F | |
| 8a.077 | N=C(CH₃)—N(CH₃)₂ | Cl | |
| 8a.078 | N=CH—CH₃ | F | |
| 8a.079 | N=CH—CH₃ | Cl | |
| 8a.080 | N=CH—C₂H₅ | F | |
| 8a.081 | N=CH—C₂H₅ | Cl | |
| 8a.082 | N=C(CH₃)—CH₃ | F | |
| 8a.083 | N=C(CH₃)—CH₃ | Cl | |
| 8a.084 | NO₂ | F | |
| 8a.085 | NO₂ | Cl | |
| 8a.086 | SO₂NH₂ | F | |
| 8a.087 | SO₂NH₂ | Cl | |
| 8a.088 | SO₂NHCH₃ | F | |
| 8a.089 | SO₂NHCH₃ | Cl | |
| 8a.090 | SO₂NHC₂H₅ | F | |
| 8a.091 | SO₂NHC₂H₅ | Cl | |

In addition, the following substituted 1-(pyridyl) pyrazoles are particularly preferred:

the compounds of the formula Ib, Nos. 1b.001–1b.091, which differ from the corresponding compounds of the formula Ia, Nos. 1a.001–1a.091 only in that the substituents chlorine and trifluoromethyl are exchanged:

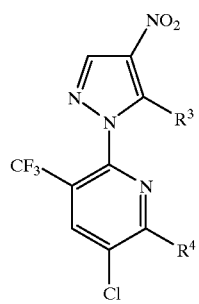

Ib the compounds of the formula IIb, Nos. 2b.001–2b.091, which differ from the corresponding compounds of the formula IIa, Nos. 2a.001–2a.091 only in that the substituents chlorine and trifluoromethyl are exchanged:

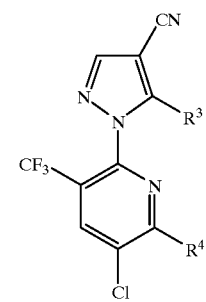

IIb the compounds of the formula IIIb, Nos. 3b.001–3b.091, which differ from the corresponding compounds of the formula IIIa, Nos. 3a.001–3a.091 only in that the substituents chlorine and trifluoromethyl are exchanged:

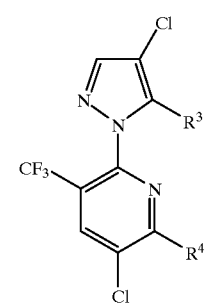

IIIb the compounds of the formula IVb, Nos. 4b.001–4b.091, which differ from the corresponding compounds of the formula IVa, Nos. 4a.001–4a.091 only in that the substituents chlorine and trifluoromethyl are exchanged:

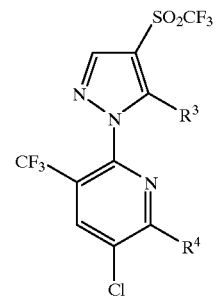

IVb the compounds of the formula Vb, Nos. 5b.001–5b.091, which differ from the corresponding compounds of the formula Va, Nos. 5a.001–5a.091 only in that the substituents chlorine and trifluoromethyl are exchanged:

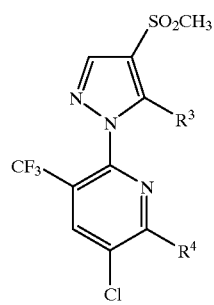

Vb the compounds of the formula VIb, Nos. 6b.001–6b.091, which differ from the corresponding compounds of the formula VIa, Nos. 6a.001–6a.091 only in that the substituents chlorine and trifluoromethyl are exchanged:

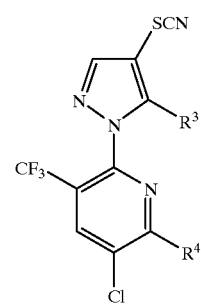

VIb the compounds of the formula VIIb, Nos. 7b.001–7b.091, which differ from the corresponding compounds of the formula VIIa, Nos. 7a.001–7a.091 only in that the substituents chlorine and trifluoromethyl are exchanged:

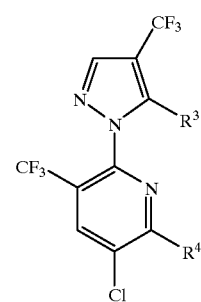

VIIb the compounds of the formula VIIIb, Nos. 8b.001–8b.091, which differ from the corresponding compounds of the formula VIIIa, Nos. 8a.001–8a.091 only in that the substituents chlorine and trifluoromethyl are exchanged:

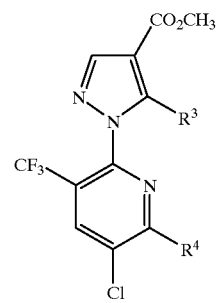

VIIIb the compounds of the formulae Ic and Id, which differ from the corresponding compounds of the formulae Ia, Nos. 1a.001–1a.091 and Ib, Nos. 1b.001–1b.091 only in that $R^4$ is methoxy:

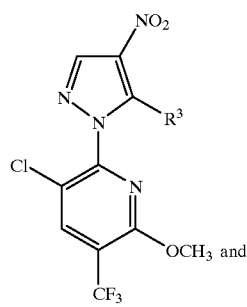

Ic and

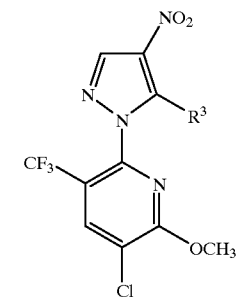

Id the compounds of the formulae IIc and IId, which differ from the corresponding compounds of the formulae IIa, Nos. 2a.001–2a.091 and IIb, Nos. 2b.001–2b.091 only in that $R^4$ is methoxy:

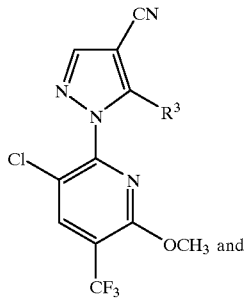

IIc and

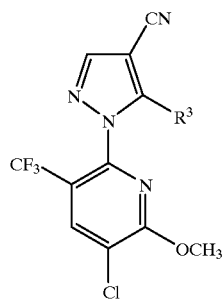
IId the compounds of the formulae IIIc and IIId, which differ from the corresponding compounds of the formulae IIIa, Nos. 3a.001–3a.091 and IIIb, Nos. 3b.001–3b.091 only in that $R^4$ is methoxy:

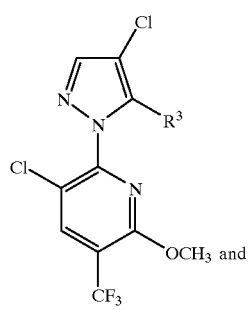
IIIc

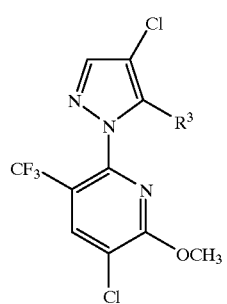
IIId the compounds of the formulae IVc and IVd, which differ from the corresponding compounds of the formulae IVa, Nos. 4a.001–4a.091 and IVb, Nos. 4b.001–4b.091 only in that $R^4$ is methoxy:

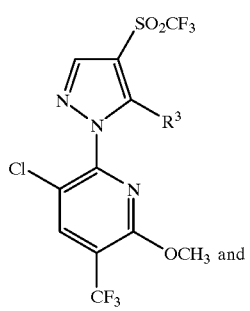
IVc

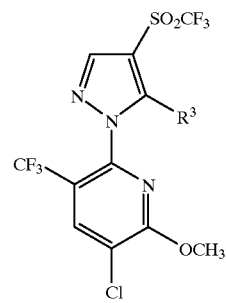
IVd the compounds of the formulae Vc and Vd, which differ from the corresponding compounds of the formulae Va, Nos. 5a.001–5a.091 and Vb, Nos. 5b.001–5b.091 only in that $R^4$ is methoxy:

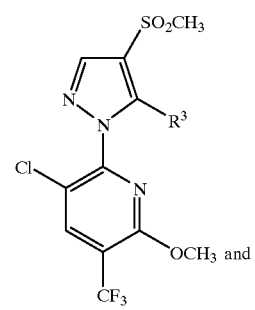
Vc

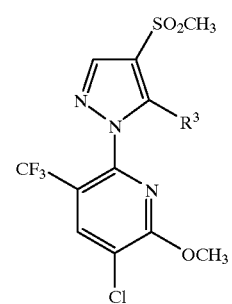
Vd the compounds of the formulae VIc and VId, which differ from the corresponding compounds of the formulae VIa, Nos. 6a.001–6a.091 and VIb, Nos. 6b.001–6b.091 only in that $R^4$ is methoxy:

VIc

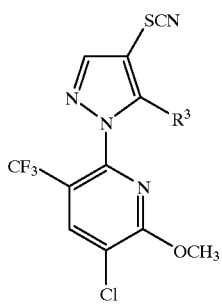
VId the compounds of the formulae VIIc and VIId, which differ from the corresponding compounds of the formulae VIIa, Nos. 7a.001–7a.091 and VIIb, Nos. 7b.001–7b.091 only in that $R^4$ is methoxy:

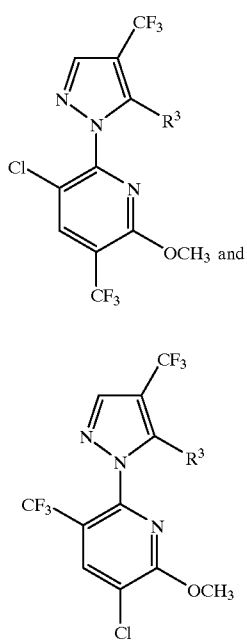

VIIc

VIId the compounds of the formulae VIIIc and VIIId, which differ from the corresponding compounds of the formulae VIIIa, Nos. 8a.001–8a.091 and VIIIb, Nos. 8b.001–8b.091 only in that $R^4$ is methoxy:

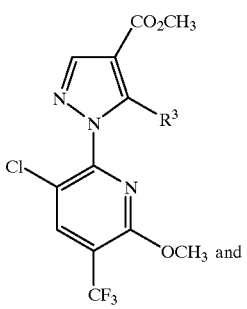

VIIIc

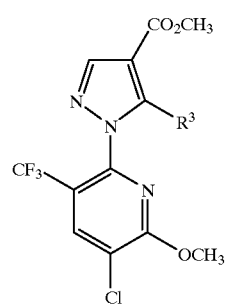

VIIId and the other compounds of the formula I described in Table 9

The 1-(pyridyl)pyrazoles of the formula I are obtainable in various ways, for example by one of the following processes:

Process A:

Reaction of a pyridyl-2-hydrazine of the formula IX, in which $R^4$ to $R^6$ have the abovementioned meanings, with an acrylonitrile derivative of the formula X according to DBP 3520 330:

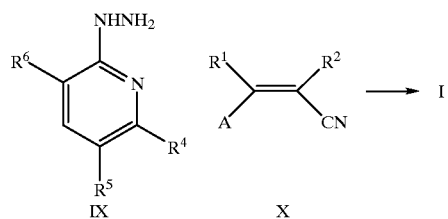

$R^1$ and $R^2$ here have the meanings given above and A is halogen, hydroxyl, alkoxy or dialkylamino.

The reaction is customarily carried out in an inert solvent or diluent, in particular in a halogenated hydrocarbon such as dichloromethane or 1,2-dichloromethane, an alcohol such as methanol, ethanol, n-propanol, isopropanol, n-butanol, glycol, methoxyethanol, ethoxyethanol or methoxypropanol, or an ether such as tetrahydrofuran, methyl tert-butyl ether, 1,2-dimethoxyethane or 1,2-diethoxyethane. The reaction temperature is normally 0–180° C., preferably 60–140° C.

The components are customarily employed in approximately stoichiometric amounts, but an excess of one of the components can be advantageous, eg. with respect to a reaction of the other components which is as complete as possible.

The hydrazines of the trifluoromethylpyridines of the general formula IXa or IXb

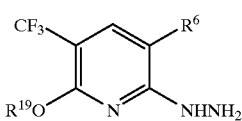

IXa

IXb

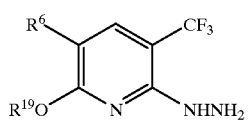

where $R^6$ and $R^{19}$ have the abovementioned meanings are obtained, for example, when 2,3,6-trichloro-5-trifluoromethylpyridine of the general formula XI

XI

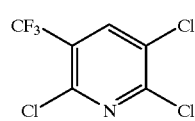

is subjected in a first step to a halogen exchange to give the corresponding 3-chloro-2,6-difluoro-5-trifluoromethylpyridine of the following formula XII

XII

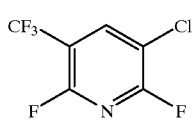

and this is then reacted successively with hydrazine to give the 2-hydrazino-3-chloro-6-fluoro-5-trifluoromethylpyridine of the following formula XIII

XIII

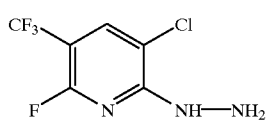

and finally with an alcohol of the general formula XIV
HO-$R^{19}$  XIV
where $R^{19}$ has the abovementioned meaning, or its alkali metal or alkaline earth metal salt to give the compounds of the formula IXa, where $R^6$ is chlorine and $R^{19}$ has the abovementioned meaning, or when, for the preparation of the compounds of the formula IXb, where $R^6$ is chlorine and $R^{19}$ has the abovementioned meaning, the above-obtained 3-chloro-2,6-difluoro-5-trifluoromethylpyridine of the following formula XII

XII

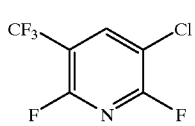

is reacted successively, first with an alcohol of the following formula XIV

HO-$R^{19}$  XIV where $R^{19}$ has the abovementioned meaning, or its alkali metal or alkaline earth metal salt to give the compounds of the following formula

XV

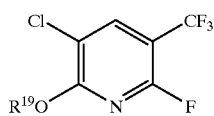

and finally with hydrazine.

It was furthermore found that the compounds of the formula IXb can also be obtained by first reacting 2,3,6-trichloro-5-trifluoromethylpyridine of the following formula XI

XI

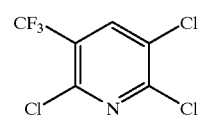

with an alcohol of the following formula XIV

HO—$R^{19}$  XIV where $R^{19}$ has the abovementioned meaning, to give the compounds of the general formula XVI

XVI

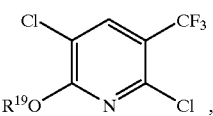

then subjecting these to a halogen exchange to give the compounds of the following formula XV

XV

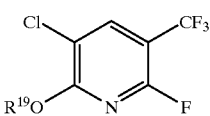

where $R^{19}$ has the abovementioned meaning, and last reacting these as described with hydrazine to give the final substances IXb, where $R^6$ is chlorine and $R^{19}$ has the abovementioned meaning.

It was furthermore found, in the case of the preparation of the 2-alkoxy-3-chloro-6-hydrazino-5-trifluoromethylpyridines and heir unsaturated analogs as further representatives of the intermediates IXb, that these can also be obtained by reacting the compounds of the general formula XVI

XVI

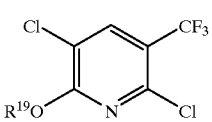

where $R^{19}$ has the abovementioned meaning, directly with hydrazine without previously carrying out a halogen exchange.

In the case of the preparation of the compounds IXa using 2,3,6-trichloro-5-trifluoromethylpyridine and potassium fluoride as halogenating agents, and the nucleophiles hydrazine and methanol, the reaction can be described by the following scheme:

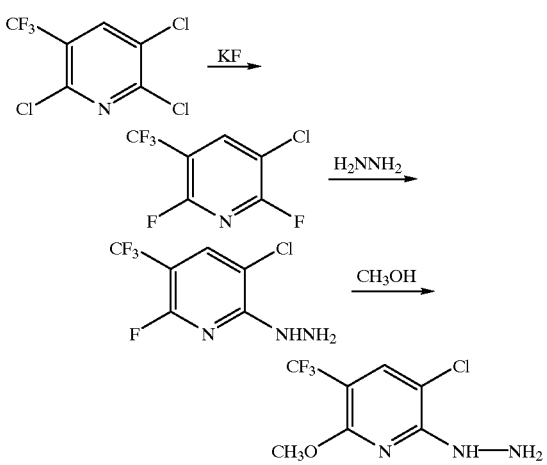

In the case of the preparation of the compounds IXb, the reaction likewise proceeds on the basis of 3-chloro-2,6-difluoro-5-trifluoromethylpyridine using, for example, methanol and hydrazine according to the following scheme:

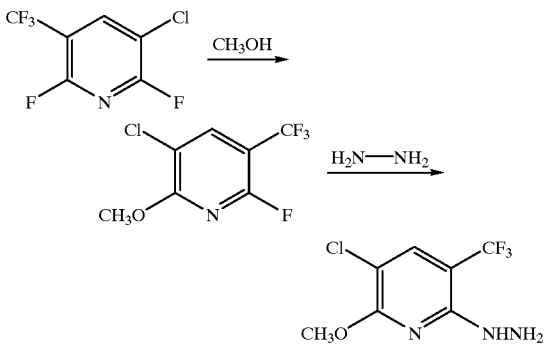

Alternatively, for the preparation of the compounds IXb, 2,3,6-trichloro-5-trifluoromethylpyridine and, for example, propargyl alcohol can be used as starting materials, then a halogen exchange can be carried out and the products can finally be reacted with hydrazine according to the following scheme:

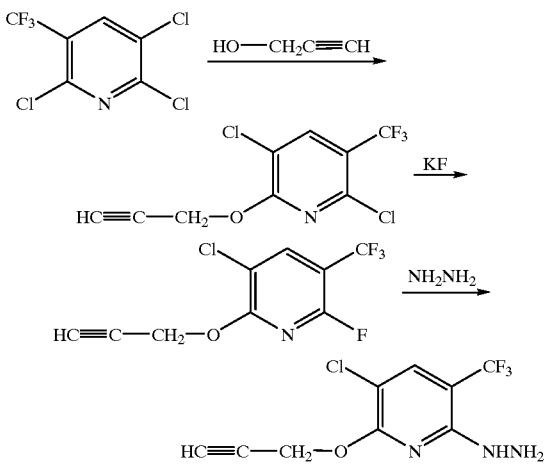

The process yields novel 2-hydrazinohalotrifluoromethylpyridines in high yield and purity in a simple and economical way. Contrary to expectation, the trifluoromethyl group is not hydrolyzed, nor is an alkoxy group already introduced eliminated again by ammonia.

The novel substituted pyridines IXa and IXb are obtainable in various ways, preferably by one of the following processes:

The halogen exchange of 2,3,6-trichloro-5-trifluoromethylpyridine is preferably carried out in the presence of a polar solvent using potassium fluoride at 100–180° C., preferably 130–170° C.

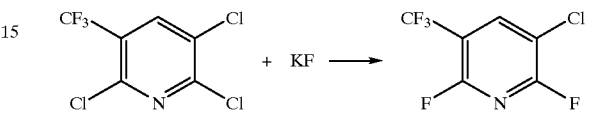

Solvents used for these reactions are nitriles such as acetonitrile, propionitrile, butyronitrile and isobutyronitrile, glycol ethers such as dimethyl glycol ether, diethyl glycol ether and diethylene glycol dimethyl ether, carboxamides such as DMF, N-methylpyrrolidone, ureas such as tetraethylurea, tetrabutylurea, dimethylethyleneurea and dimethylpropyleneurea, sulfoxides such as dimethyl sulfoxide and preferably sulfones such as dimethyl sulfone, diethyl sulfone, tetramethylene sulfone (sulfolane) or pentamethylene sulfone. Carrying out the reaction in the melt without addition of a solvent is also possible according to the invention.

Halogen exchange proceeds at a high rate even without a catalyst. However, it can be accelerated by a catalyst, for example a crown ether or cryptand. These are organic complex ligands which serve particularly well for the binding of alkali. The cryptands yield a three-dimensional envelope. With respect to the preparation of these substances, see Konkakte [Contact Catalysts] (1977), pages 11–31 and 36–48. Preferred catalysts are crown ethers, of which, for example, the following compounds should be mentioned: 12-crown-4, 14-crown-4, dibenzo-14-crown-4, 18-crown-5, 18-crown-6, dibenzo-18-crown-6 or aza-18-crown-6.

These catalysts are expediently employed in an amount from 0.05–5, in particular 0.1–2 mol percent per mole of starting substance.

The molar ratios in which the starting compounds are reacted with one another are 1.9–2.8, preferably 2–2.4 for the ratio of potassium fluoride to pyridine derivative. The concentration of the starting materials in the solvent is 0.1–5 mol/l, preferably 0.2–2 mol/l.

The compound 3-chloro-2,6-difluoro-5-trifluoromethylpyridine can be prepared particularly advantageously if, before the actual halogen exchange, the 2,3,6-trichloro-5-trifluoromethylpyridine is treated, for example, in the presence of an aliphatic sulfone at up to 150° C., expediently from 50° C. to 120° C., in particular 70–100° C. with 0.1–0.4, expediently 0.15–0.3, mol of an acid chloride of sulfurous acid or carbonic acid and the reaction mixture is then reacted at 70–250° C., preferably 80–200° C., with potassium fluoride.

Suitable catalysts for this process stage are, for example, N,N-disubstituted carboxamides such as DMF, N,N-dimethylacetamide or N,N-diisopropylacetamide. The catalyst is expediently employed in an amount of 0.2–2 percent by weight based on the acid chloride.

In the reaction with the acid chloride, heating is expediently carried out until evolution of gas no longer takes place.

It is recommended to remove excess acid chloride, eg. by blowing in an inert gas, such as nitrogen, or by applying vacuum.

The potassium fluoride, which has expediently been predried, is then added to this mixture and the mixture obtained by stirring is kept at reaction temperature for 1–10 hours.

In addition to potassium fluoride, possible fluoride salts according to the invention are also tetraalkyl-($C_1$–$C_{13}$)-ammonium fluoride and corresponding mixtures with one another or with cesium fluoride or rubidium fluoride, these mixtures with cesium fluoride containing not more than 50% by weight of cesium fluoride. Fluoride mixtures are preferably used which contain at least 75% by weight of potassium fluoride; in particular, mixtures of this type consist of at least 90% by weight of potassium fluoride and at most 10% by weight of cesium fluoride or of 60% by weight of potassium fluoride and 40% by weight of rubidium fluoride. In a further preferred embodiment, only potassium fluoride is used as fluoride salt.

The phase-transfer catalysts used can be quaternary ammonium or phosphonium salts. Suitable compounds which may be mentioned are the following: tetraalkyl-($C_1$–$C_{18}$)-ammonium chlorides, bromides or fluorides, tetraalkyl-($C_1$–$C_{18}$)-phosphonium chlorides or bromides, tetraphenylphosphonium chloride or bromide, $(phenyl)_m$ $(alkyl$-($C_1$–$C_{18}$))n-phosphonium chlorides or bromides, where m=1–3, n=3–1 and m+n=4. Mixtures of these salts can also be employed. On suitable choice of the catalyst for the particular compound to be reacted, which can easily be determined by a few routine tests, high space efficiencies and yields are obtained; the apparatus dead times and the total apparatus costs in the process according to the invention are additionally particularly favorable.

The amount of phase transfer catalyst is in general up to 20% by weight, preferably from 3 to 15% by weight and particularly preferably from 3–8% by weight, based on the amount of fluoride salt employed.

The phase transfer catalysts used can also be oligo- or polyalkylene glycol dimethyl ethers, the alkylene radical containing 2–6 C atoms, preferably 2 or 3 C atoms, ie. preferably represents the ethylene or the propylene radical and in particular only the ethylene radical. The number of O-ethylene (glycol) units ($—O—CH_2—CH_2—$)$_n$ and/or of O-propylene units in these compounds can be from n=4 (eg. tetraethylene glycol dimethyl ether) to about n=150; but preferably ethers are employed whose degree of polymerization is from n=4 to n=25. In the case of alkylene radicals having more than 3 C atoms, n is in general not higher than 6. The amount of these ethers used, in particular glycol ethers, is usually from approximately 0.6% by weight to approximately 200% by weight, preferably from approximately 5 to approximately 100% by weight and particularly preferably from approximately 10 to approximately 50% by weight, based on the amount of the fluoride salt employed. The particular advantage in the use of these compounds is that usually, corresponding to the amount used, less solvent can be used, as the glycol ethers are generally liquid at the reaction temperature. Mixtures of these ethers with one another and mixtures of these ethers (individually or as mixtures) with the quaternary ammonium or phosphonium salts, preferably glycol ethers with quaternary phosphonium salts, can also be employed.

If, as fluoride salt, tetraalkyl-($C_1$–$C_{18}$)-ammonium fluorides are used, the addition of a further phase transfer catalyst is not necessary, as the fluoride salt itself is one of those which can be employed therewith, for example, in stoichiometric and relatively large amounts.

The use of spray-dried alkali metal fluoride in the process according to the invention does in this case shorten the reaction times to some extent, but is not absolutely necessary. The reaction can also be carried out with addition of acid acceptors, such as alkali metal and alkaline earth metal carbonates or basic oxides, for example magnesium oxide, or corresponding mixtures. Particularly preferred in this context is potassium carbonate, which is used in amounts of approximately 1–approximately 10% by weight, preferably of approximately 4–approximately 6% by weight, based on the amount of fluoride salt.

The acid acceptors are in general not essential for the course of the reaction. In some cases, the reaction rate is considerably decreased by the formation of hydrogen fluoride during the reaction. In these cases, it is favorable, particularly also to avoid apparatus corrosion, to work in the presence of acid scavengers of this type. The use of these compounds in fractionation of the reaction mixture or of the crude product may be desirable for reasons of corrosion in the fractionating unit, magnesium oxide being particularly preferred in this context. For this purpose, up to approximately 10% by weight of acid scavenger is added to the fractionating still, preferably from approximately 3 to 8% by weight, based on the total amount of distillation bottom employed.

After reaction with alkali metal fluoride, the mixture is worked up in a customary manner, eg. by filtering, washing the solid material and distilling the filtrates and wash filtrates. In the case of water-miscible solvents, the pyridine derivatives XII or XV can also be precipitated by adding water and worked up as described.

The reaction of the 2,6-difluoropyridine and of the 2-fluoropyridines with hydrazine or of the 2,5-dichloropyridines with hydrazine can be performed in the absence or, advantageously, in the presence of a solvent. Suitable solvents are, in particular, those listed below:

hydrocarbons, eg. pentane, hexane, heptane, cyclohexane, alcohols, eg. methanol, ethanol, n-propanol, isopropanol, butanol and isobutanol, ethers such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters such as ethyl acetate, n-butyl acetate and isobutyl acetate, chlorinated hydrocarbons such as methylene chloride, 1,1,2,2-tetrachloroethane, 1,1-dichloroethylene, 1,2-dichloroethane, chlorobenzene, 1,2-, 1,3- and 1,4-dichlorobenzene, 1-chloronaphthalene and 1,2, 4-trichlorobenzene, nitrohydrocarbons such as nitromethane, nitroethane, nitropropane and nitrobenzene, dipolar aprotic solvents, eg. acetonitrile, propionitrile, dimethylformamide, dimethylacetamide, dimethyl sulfoxide, N-methylpyrrolidone, 1,3-dimethyltetrahydro-2-(1H)-pyrimidinone and 1,3-dimethyl imidazolidin-2-one, aromatics, eg. benzene, toluene and xylene or heteroaromatics, eg. pyridine, α,β,γ-picoline and quinoline, or water and mixtures of these solvents.

Expediently, the solvent is used in an amount of 100–2000% by weight, preferably 400–1200% by weight, based on the starting substances XII, XV or XVI.

Advantageously, 0.9–10, in particular 1.1–5, mol equivalents of hydrazine hydrate, based on the starting substances are added in the course of 0.25–2 hours to a mixture of the starting substances in one of the abovementioned solvents at 0–180° C., preferably 10–130° C., and the mixture is stirred until completion of the reaction (about 2–20 hours).

If only approximately stoichiometric amounts of hydrazine are employed, an organic auxiliary base is expediently additionally used to trap the hydrogen halide formed. Suitable auxiliary bases for this purpose are customary organic bases such as trimethylamine, triethylamine, N-ethyldiisopropylamine, triisopropylamine, N,N-dimethylaniline, N,N-dimethylcyclohexylamine, N-methylpyrrolidine, pyridine, quinoline, α,β,γ-picoline, 2,4- and 2,6-lutidine and triethylenediamine. The auxiliary base used, however, can also be inorganic basic substances, eg. an alkali metal or alkaline earth metal hydroxide such as lithium, sodium, potassium, calcium, magnesium or zinc hydroxide or an alkali metal or alkaline earth metal hydrogen carbonate or carbonate of the same cations mentioned above. In general, additions of 0.9–1.1 equivalents of the auxiliary base, based on the starting substances XII, XV or XVI, are sufficient.

The reaction can be carried out continuously or batchwise without pressure or under pressure.

Working up can be carried out in a customary manner, eg. the reaction mixture is extracted with water to remove the salts and dried, and the organic phase is purified, for example by chromatography or distillation. However, the organic phase can also be concentrated directly and the residue stirred with a solvent.

The reaction of the 2,6-dichloropyridines, the 2,6-difluoropyridines and the 2-hydrazinopyridines with an alcohol or its salt can be performed in the absence or, advantageously, in the presence of a solvent. The solvents employed can be the abovementioned, and further, ketones, eg. acetone, methyl ethyl ketone or appropriate mixtures; however, the alcohol used can also be used directly as a solvent.

Expediently, the solvent is used in an amount of 100–2000% by weight, preferably 400–1200% by weight, based on the starting substances XI, XII or XIII.

To bind the hydrogen halide eliminated in the reaction, an alkali metal or alkaline earth metal hydroxide such as lithium, sodium, potassium, calcium, magnesium or zinc hydroxide, an alkali metal or alkaline earth metal hydrogencarbonate or carbonate of the same cations mentioned above or a metal alkoxide, for example a lithium, sodium or potassium alkoxide, is expediently added. The alkoxides are expediently prepared in situ by dissolving the abovementioned metals in the alcohol to be employed or by the action of lithium, sodium, potassium or calcium hydride. However, one of the abovementioned organic auxiliary bases can also be used.

Advantageously, 0.8–1.5, in particular 0.9–1.2, mol equivalents of the alcohol are expediently added to a mixture of the starting substances XI, XII or XIII in one of the abovementioned solvents at −20–100° C., preferably 0–30° C., in the presence of an equivalent amount (of a base) or of the corresponding alkoxide in the course of 0.25–0.5 hours and the mixture is stirred for a further 1–12 hours at 10–120° C., preferably 2–10 hours at 20–80° C., until the reaction is complete, and then worked up. However, conversely, the alcohol can also be added to the solvent together with a base or the corresponding alkoxide and the starting substances then added under the above conditions.

The reaction can be carried out continuously or batchwise without pressure or under pressure.

Working up can be carried out in the same manner as described for the reaction of the starting substances.
Process B:

Hydrolysis and decarboxylation of a 1-(2-pyridyl) pyrazole-4-carboxylic ester of the formula Ie, in which $R^1$ to $R^6$ have the abovementioned meanings, according to DBP 3520 330.

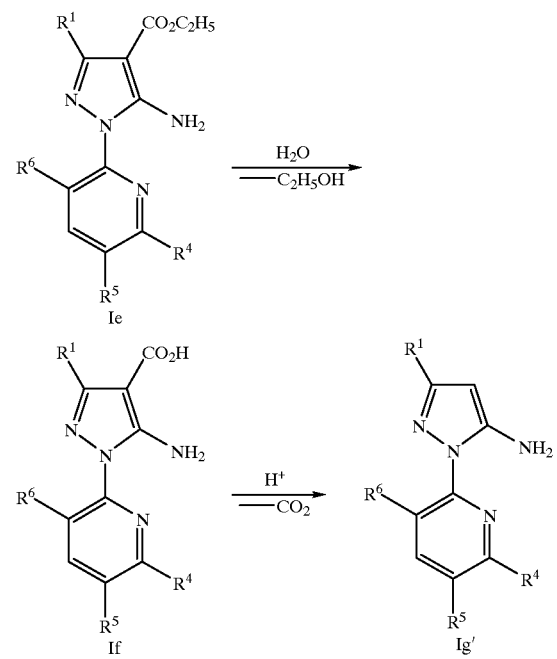

To this end, a 1-(2-pyridyl)pyrazole-4-carboxylic ester can be hydrolyzed for 1–6 hours at 40–100° C., advantageously 70–90° C. with dilute aqueous alkali solution, if appropriate in the presence of aqueous alcohol as solubilizer, and then isolated by acidifying the carboxylic acid If. By treatment with dilute hydrohalic acid, expediently in the presence of a lower alcohol as solubilizer, at 60–120° C., advantageously 70–90° C., the pyrazole derivative Ig' is then obtained.

However, the pyrazole ester of the formula Ie can also be treated directly with aqueous hydrobromic acid at 60–120° C., advantageously 70–90° C., until the hydrolysis and decarboxylation to give Ig' is complete.

Suitable alkali solutions are sodium hydroxide solution and potassium hydroxide solution. Suitable alcohols are methanol, ethanol, n-propanol, isopropanol or n-butanol.

Suitable hydrohalic acids are hydrochloric, hydrobromic or hydriodic acid.
Process C:

Reaction of a 1-(2-pyridyl)-5-aminopyrazole Ig with a reactive sulfur-halogen compound XVII or a reactive carbonic acid compound XVIII or a reactive amide acetal XIX

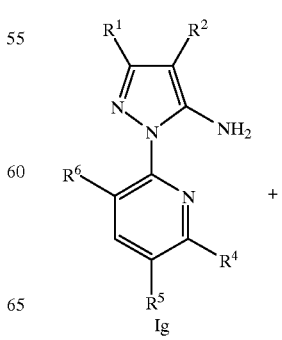

+

-continued

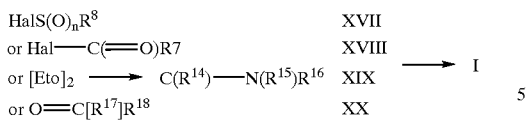

or a reactive keto compound XX according to DBP 3520330:

In the formula Ig, representing I and XVII to XX, $R^1$ to $R^{18}$ preferably are those radicals which have already been mentioned as preferred for these substituents in connection with the description of the substances of the formula I according to the invention. Halogen is fluorine, chlorine or bromine, preferably chlorine or bromine.

The reaction is customarily carried out in an inert solvent or diluent, in particular a halogenated hydrocarbon such as dichloromethane or 1,2-dichloroethane, an ether such as diethyl ether, methyl tert-butyl ether, tetrahydrofuran, 1,4-dioxane or anisole, a nitrile such as acetonitrile, propionitrile or butyronitrile, an ester such as ethyl acetate, methyl or ethyl propionate or, if the presence of water does not interfere, if appropriate also in a two-phase mixture with water.

To bind the hydrogen halide liberated during the reaction with the starting substances XVII–XVIII, bases are expediently employed, for example alkali metal carbonates and hydrogencarbonates such as sodium hydrogencarbonate, potassium hydrogencarbonate, sodium carbonate and potassium carbonate, alkali metal alkoxides such as sodium methoxide and potassium tert-butoxide, alkali metal hydroxides such as sodium hydroxide or potassium hydroxide. Advantageously, organic bases are also suitable: trimethylamine, triethylamine, pyridine, α,β,γ-picoline, lutidine, N,N-dimethylaniline, N,N-diethylaniline, N-propylpiperidine, quinoline, isoquinoline, quinazoline, quinoxaline, triethanolamine, triamylamine, tri-n-butylamine, trifurfurylamine, trihexylamine, N-methylimidazole, N-methylpyrrole, N-ethylpiperidine, N-methylpyrrolidine, pyrazine, pyrimidine, acridine, phenanthridine, phenazine, N,N-dimethylcyclohexylamine or N-propyldiisopropylamine.

During reaction of the reactive amide acetals XIX or of the keto compound XX, the stirring of the starting substances, if appropriate with removal of the eliminated alcohol or of the water of reaction by distillation or warming on a water separator, is sufficient. The reaction temperature is normally 0–120° C., preferably 20–80° C.

The components are customarily employed in approximately stoichiometric amounts, but an excess of one of the components may also be advantageous, eg. with respect to the reaction of the other components which is as complete as possible.

If an excess of the starting substances XVII–XVIII is specifically employed, but at least 2 equivalents per molee of starting substance Ig, a substitution of both amino hydrogens occurs.

Process D:

Reaction of a 1-(2-pyridyl)pyrazole of the formula Ig', in which $R^1$ and $R^3$ to $R^6$ have the abovementioned meanings, with electrophilic agents of the formula XXI, in which B is an electron-with-drawing leaving group, according to DE 35 20 330, Jo 2142- 785 or EP 201 852:

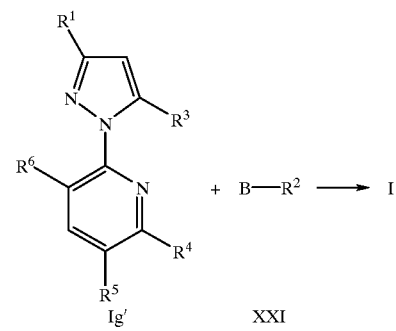

Here, the radical $R^2$ in the general formula XXI is preferably chlorine, bromine, nitro, thiocyanato, formyl, alkanoyl having 1–4 carbon atoms in the alkyl moiety, $C_1$–$C_4$-alkylsulfonyl, -sulfinyl or -sulfenyl or halomethylsulfenyl.

B is preferably halogen, in particular chlorine or bromine, hydroxyl, alkyl- or arylsulfonyloxy, or alkanoyloxy or aroyloxy. Further electrophilic agents are sulfuryl chloride, phosphorus oxychloride/dimethylformamide, nitrating acid and other substances which can customarily be used for electrophilic substitution.

The reaction is customarily carried out in one of the abovementioned inert solvents or diluents.

The reaction temperature is normally 0–150° C., preferably 10–110° C.

Process E:

Diazotization of 1-(2-pyridyl)-5-aminopyrazole of the formula Ih, in which $R^1$, $R^2$ and $R^4$ to $R^6$ have the abovementioned meanings, and subsequent boiling to give the corresponding 5-hydroxy compound according to Houben-Weyl, "Methoden der organischen Chemie" [Methods of Organic Chemistry] IVth Edition, Vol. 6/1C, p. 247, Georg Thieme Verlag, Stuttgart 1968, or reaction to give the corresponding fluoro compounds, ibid Vol. 5/3, p. 213, reaction under Sandmeyer conditions to give the corresponding chloro compounds, ibid Vol. 5/3, p. 846, bromo compounds, ibid Vol. 5/4, p. 437 or iodo compounds, ibid Vol. 5/4, p. 639,

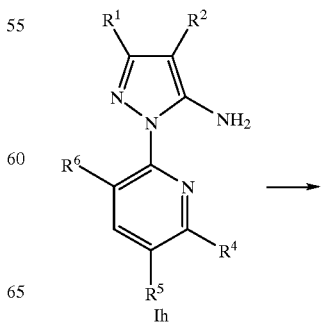

-continued

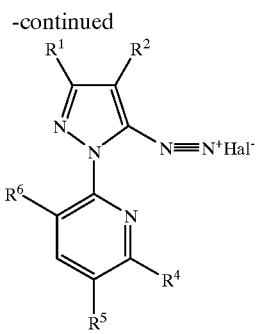

or reaction to give the corresponding cyano compounds, ibid Vol. 8, p. 311 or thiocyanato compounds, ibid Vol. 9, p. 863, or reaction under Meerwein conditions to give the corresponding sulfonyl chlorides, ibid Vol. 9, p. 579 and subsequent reaction with ammonia or amines according to the Schotten-Baumann reaction, ibid Vol. 9, p. 609 or reaction with mercaptans to give the corresponding thioethers, ibid Vol. 9, p. 116 or with alcohols to give the corresponding ethers, ibid Vol. 6/3, p. 81.

Process F:

Reaction of a 1-(2-pyridyl)-5-halopyrazole of the formula Ii, in which halogen, $R^1$, $R^2$ and $R^4$ to $R^6$ have the abovementioned meanings, with amines of the formula XXII, in which $R^{10}$ and $R^{11}$ have the abovementioned meanings,

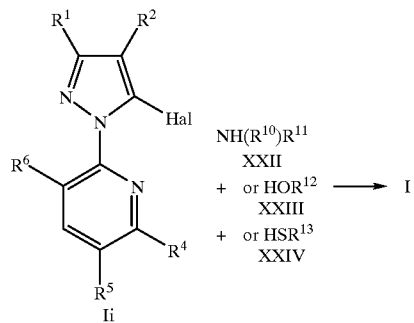

with alcohols of the formula XXIII, in which $R^{12}$ has the abovementioned meanings, and with mercaptans of the formula XXIV, in which $R^{13}$ has the abovementioned meanings, according to a similar process.

To carry out the process, in general 1.0–5.0 mol, preferably 1.0–2.0 mol, of the nucleophiles XXII–XXIV are employed per mole of 5-halopyrazole Ii. The reaction is carried out and worked up and the reaction products I are isolated by generally customary processes.

Suitable diluents for carrying out process F are inert organic solvents. Those preferably used are aliphatic or aromatic, unhalogenated or halogenated hydrocarbons, such as pentane, hexane, heptane, cyclohexane, petroleum ether, toluene, xylene, methylene chloride, 1,2-dichloroethane, chlorobenzene or dichlorobenzene, ethers such as diethyl ether, diisopropyl ether, methyl tertbutyl ether, ethylene glycol dimethyl ether, tetrahydrofuran or dioxane, esters such as ethyl acetate, nitriles such as acetonitrile or propionitrile or amides such as dimethylformamide, dimethylacetamide or N-methylpyrrolidone.

Finally, however, the nucleophiles of the formulae XXII–XXIV used as reaction components can also be employed simultaneously as diluents in an appropriate excess.

If appropriate, the process can be carried out in the presence of a basic catalyst to remove the hydrogen halide formed. Those which are suitable are all customary inorganic or organic bases. Preferably, the bases mentioned in process C are used.

However, the alkali metal or alkaline earth metal salts of the nucleophiles XXII–XXIV can also be employed directly, preferably the lithium, sodium, potassium, magnesium or calcium salts.

The temperatures in process F can be varied within a relatively wide range. In general, the reaction is carried out at from 0 to 150° C., preferably from 20 to 100° C.

Process G:

Reaction of a 1-(6-halo-2-pyridyl)pyrazole of the formula Ik, in which $R^1$ to $R^3$ and $R^5$ and $R^6$ have the abovementioned meanings, with a nucleophile of the formula XXV, in which X is oxygen or sulfur and $R^{19}$ has the abovementioned meanings:

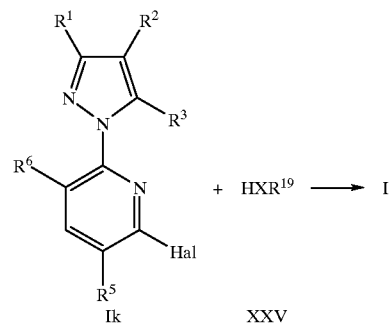

To carry out the process according to the invention, in general 0.8–2.0 mol, preferably 0.9–1.3 mol, of the nucleophile XXV are employed per mole of 1-(6-halo-2-pyridyl) pyrazole Ik.

Suitable diluents for carrying out process G are the solvents described in process F.

However, the nucleophile of the formula XXV used as a reaction component can also be employed simultaneously as a diluent in an appropriate excess.

If appropriate, the process can be carried out in the presence of a basic catalyst to remove the hydrogen halide formed. Those which are suitable are all customary inorganic or organic bases. Preferably, the bases mentioned in process C are used.

However, the alkali metal or alkaline earth metal salts of the nucleophiles XXV can also be employed directly, preferably the lithium, sodium, potassium, magnesium or calcium salts.

The temperatures in process G can be varied within a relatively wide range. In general, the reaction is carried out at from 0 to 150° C., preferably from 10 to 80° C.

The reaction is carried out and worked up and the reaction products I are isolated by generally customary processes.

Process H:

Alternatively to the previous processes, the 6-halo radical of the 2-pyridyl substituent in the general formula Ik can also be introduced by first converting a 1-(2-pyridyl) pyrazole Il, in which $R^1$ to $R^3$ and $R^5$ and $R^6$ have the abovementioned meanings, into its N-oxide using an oxidant and then rearranging with a phosphorus oxyhalide, for example phosphorus oxychloride, to give the 6-chloro-2-pyridyl compound Ik'.

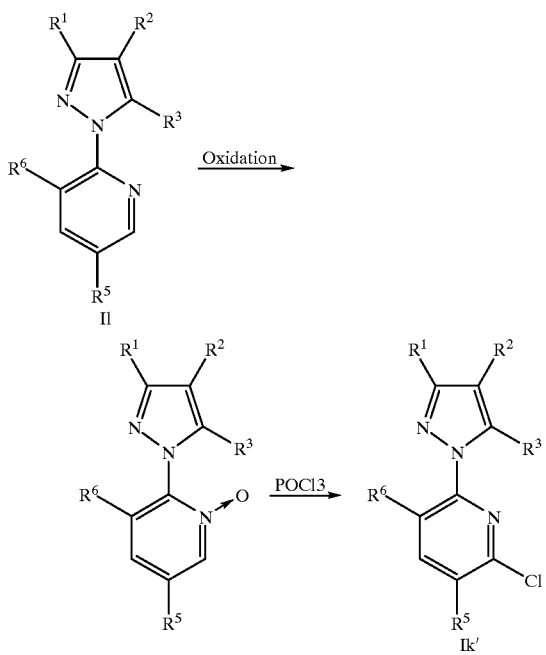

The oxidant used is, for example, m-chloroperbenzoic acid or hydrogen peroxide in an inert solvent, for example one of the abovementioned halohydrocarbons such as methylene chloride or an alkanecarboxylic acid such as glacial acetic acid or trifluoroacetic acid.

The oxidation is in general carried out at 0–100° C., preferably 20–60° C., and the reaction with the phosphorus oxyhalide is carried out at 80–120° C.

The molar ratios in which the starting compounds required are reacted with one another are in general from 1:0.9 to 1:1.5 for the ratio of 1-(2-pyridyl)pyrazole Il to the oxidant. In the subsequent halogenation step an inert solvent such as chlorobenzene can be used, but the reaction is expediently carried out directly in excess phosphorus oxyhalide as reaction medium.

The concentration of the starting materials in the solvent (mixture) is in general 0.1–5 mol/l, preferably 0.2–2 mol/l.

The individual process steps are known from the literature or can be carried out by methods generally known from the literature (J. Org. Chem, Vol. 19, 1633 (1954), EP 422 456).

If not stated otherwise, all processes described above are expediently performed at atmospheric pressure or under the autogenous pressure of the particular reaction mixture.

The reaction mixtures are generally worked up by methods known per se, for example by removing the solvent, partitioning the residue in a mixture of water and a suitable organic solvent and working up the organic phase to the product.

1-(Pyridyl)pyrazoles I having CH-acidic substituents can be converted in a manner known per se into their salts, preferably into their alkali metal salts.

Salts of I whose metal ion is not an alkali metal ion can be prepared by double decomposition of the corresponding alkali metal salt in a customary manner, just like ammonium and phosphonium salts can be prepared by means of ammonia, phosphonium, sulfonium or sulfoxonium hydroxides.

Compounds I which carry a terminal amino group can further form acid addition salts. Generally the salts of those acids which also do not adversely affect the herbicidal action of I are suitable, ie., for example, the hydrochlorides and hydrobromides, sulfates, nitrates, phosphates, oxalates or dodecylbenzenesulfonates.

Synthesis of the precursors 2,5-Dichloro-6-methoxy-3-trifluoromethylpyridine 10.8 g (0.06 mol) of 30% strength sodium methoxide solution were added to 15 g (0.06 mol) of 2,3,6-trichloro-5-trifluoromethylpyridine in 200 ml of methyl tert-butyl ether at 0–5° C. with stirring in the course of 20 minutes and the mixture was subsequently stirred at the same temperature for 30 minutes. After warming to 20° C., the resulting fine precipitate was filtered off with suction and washed with methyl tert-butyl ether. The organic filtrate was washed with water, dried and concentrated, 14.3 g (97% of theory) of the title compound of $n^{25}_D=1.4890$ being obtained.

2,5-Dichloro-6-propargyloxy-3-trifluoromethylpyridine 9.5 g (0.3952 mol) of sodium hydride were initially introduced into 500 ml of diethyl ether while flushing with nitrogen. 50 ml of propargyl alcohol were added at 5–10° C. with stirring in the course of 30 minutes and the mixture was stirred at 20° C. for a further 30 minutes. 90 g (0.3593 mol) of 2,3,6-trichloro-5-trifluoromethylpyridine in 150 ml of diethyl ether were then added at 0–5° C. with stirring in the course of 20 minutes, a fine precipitate being formed. After warming to 20° C., the mixture was worked up as above, 96 g (99% of theory) of the title compound of $n^{24}_D=1.5038$ being obtained.

3-Chloro-2,6-difluoro-5-trifluoromethylpyridine 110.3 g (0.44 mol) of 2,3,6-trichloro-5-trifluoromethylpyridine and 58.7 g (1.01 mol) of potassium fluoride were added with stirring to 500 ml of sulfolane (as on p. 39, dried using thionyl chloride) and the mixture was stirred at 150–160° C. for 2½ hours with HPLC checking. After cooling to 50° C., 93 g (98% of theory) of the title compound were distilled off from the reaction mixture at 40–45° C., 25 mbar.

NMR (400 MHz, CDCl$_3$) 8.2 Pyr-H/t; $n^{23}_D=1.4229$.

3-Chloro-6-fluoro-2-hydrazino-5-trifluoroethylpyridine 10.5 g (0.21 mol) of hydrazine hydrate were added to a mixture of 21.8 g (0.1 mol) of 3-chloro-2,6-difluoro-5-trifluoromethylpyridine in 100 ml of propanol at 50° C. with stirring in the course of 15 minutes and it was subsequently stirred at the same temperature for 2 hours. After cooling, the reaction mixture was poured onto 1.5 ml of water and the precipitate which was deposited was filtered off with suction. To purify it, it was taken up in ethyl acetate and extracted with water. After drying and concentrating, 20.9 g (91% of theory) of the title compound of m.p. 104–106° C. were obtained; a sublimed sample melted at 111–113° C.

3-Chloro-6-fluoro-2-propargyloxy-5-trifluoromethylpyridine 47.3 g (0.175 mol) of 2,5-dichloro-6-propargyloxy-3-trifluoromethylpyridine, 0.5 g (1.89 mmol) of 18-crown-6 and 15.2 g (0.263 mol) of potassium fluoride were added to 150 ml of sulfolane and it was stirred at 150–155° C. for 5 hours. After cooling, the reaction mixture was stirred with methyl tert-butyl ether and separated off from the inorganic precipitate. The filtrate was extracted four times with water, dried and concentrated. The residue was filtered with suction with methylene chloride through a suction filter containing silica gel and concentrated, 31.4 g (71% of theory) of the title compound of $n^{24}_D$=1.4732 being obtained.

3-Chloro-6-hydrazino-2-methoxy-5-trifluoromethylpyridine 10.7 g (0.214 mol) of hydrazine hydrate were added in the course of 10 minutes with stirring at 50° C. to 25.0 g (0.102 mol) of 2,5-dichloro-6-methoxy-3-trifluoromethylpyridine in 100 ml of propanol and the mixture was stirred at 90° C. for 3 hours. After cooling, the resulting suspension was added to 1.2 liters of water, the precipitate was filtered off with suction and taken up in methylene chloride, and the solution was washed with water. The organic phase was dried and concentrated, and the residue was stirred with ether/pentane (1:1). After filtering off with suction and drying, 7.8 g (32% of theory) of the title compound of m.p. 140–142° C. were obtained.

3-Chloro-6-hydrazino-2-propargyloxy-5-trifluoromethylpyridine

Starting from 7.8 g (0.155 mol) of hydrazine hydrate and 20 g (0.074 mol) of 2,5-dichloro-6-propargyloxy-3-trifluoromethylpyridine, under the conditions of the previous example 11.0 g (56% of theory) of the title compound were obtained as a colorless powder of m.p. 98–102° C.

Further compounds IXa or IXb including their precursors XV or XVI can be prepared or were prepared according to one of the processes described:

TABLE 9

IXa

| $R^6$ | $R^6$ | $R^{19}$ | M.p. [° C.], $n^{23}_D$ |
|---|---|---|---|
| 9a.001 | Cl | $CH_3$ | |
| 9a.002 | F | $CH_3$ | |
| 9a.003 | Cl | $C_2H_5$ | |
| 9a.004 | Cl | n-$C_3H_7$ | |
| 9a.005 | Cl | i-$C_3N_7$ | |
| 9a.006 | Cl | $CH_2$—CH=$CH_2$ | |
| 9a.007 | F | $CH_2$—CH=$CH_2$ | |
| 9a.008 | Cl | $CH_2$—C≡CH | |
| 9a.009 | F | $CH_2$—C≡CH | |
| 9a.0010 | Cl | $CH_2CO_2CH_3$ | |
| 9a.0011 | Cl | CH[$CH_3$]—$CO_2CH_3$ | |
| 9a.0012 | Cl | CH[$CH_3$]—CO—NH—$CH_3$ | |

TABLE 10

IXb

| $R^6$ | $R^6$ | $R^{19}$ | M.p. [° C.], $n^{23}_D$ |
|---|---|---|---|
| 10b.001 | F | $CH_3$ | |
| 10b.002 | Cl | $C_2H_5$ | |
| 10b.003 | F | $C_2H_5$ | |

TABLE 10-continued

IXb

| $R^6$ | $R^6$ | $R^{19}$ | M.p. [° C.], $n^{23}_D$ |
|---|---|---|---|
| 10b.004 | Cl | n-$C_3N_7$ | |
| 10b.005 | F | n-$C_3N_7$ | |
| 10b.006 | Cl | i-$C_3H_7$ | |
| 10b.007 | Cl | $CH_2$—CH=$CH_2$ | |
| 10b.008 | F | $CH_2$—C≡CH | |
| 10b.009 | Cl | $CH_2CO_2CH_3$ | |
| 10b.0010 | F | $CH_2CO_2CH_3$ | |
| 10b.0011 | Cl | CH[$CH_3$]—$CO_2CH_3$ | |
| 10b.0012 | Cl | CH[$CH_3$]—$COCH_3$ | |

TABLE 11

XV Hal = F
XVI Hal = Cl

| | $R^{19}$ | $R^{19}$ | Hal | M.p. [° C.], $n^{23}_D$ |
|---|---|---|---|---|
| 11.001 | $C_2H_5$ | | Cl | 1.4835 |
| 11.002 | n-$C_3N_7$ | | Cl | 1.4808 |
| 11.003 | i-$C_3H_7$ | | Cl | 1.4760 |
| 11.004 | $CH_3$ | | F | 1.4504 |
| 11.005 | $C_2H_5$ | | F | 1.4662 |
| 11.006 | $CH_2$—CH=$CH_2$ | | Cl | |
| 11.007 | $CH_2$—C≡CH | | Cl | |
| 11.008 | $CH_2CO_2CH_3$ | | Cl | |
| 11.009 | CH[$CH_3$]—$CO_2CH_3$ | | Cl | |
| 11.0010 | CH[$CH_3$]—CO—$NHCH_3$ | | Cl | |
| 11.0011 | $CH_2CH_2OCH_3$ | | Cl | |
| 11.0012 | $CH_2CH_2CN$ | | Cl | |
| 11.0013 | $CH_2CO$—N[$CH_3$]$_2$ | | Cl | |
| 11.0014 | n-$C_3H_7$ | | F | |
| 11.0015 | $CH_2$—CH=$CH_2$ | | F | |
| 11.0016 | $CH_2$—C≡CH | | F | |
| 11.0017 | $CH_2CO_2CH_3$ | | F | |
| 11.0018 | CH[$CH_3$]—$CO_2CH_3$ | | F | |
| 11.0019 | CH[$CH_3$]—CO—$NHCH_3$ | | F | |
| 11.0020 | $CH_2CH_2OCH_3$ | | F | |
| 11.0021 | $CH_2CH_2CN$ | | F | |
| 11.0022 | $CH_2CO$—N[$CH_3$]$_2$ | | F | |

EXAMPLE 1

4-Nitro-5-propionamido-1-(3,6-dichloro-5-trifluoromethyl-2-pyridyl)pyrazole a) 2.8 g (0.0413 mol) of 50% strength hydrogen peroxide were added to a mixture of 10 g (0.0275 mol) of 4-nitro-5-propionamido-1-(3-chloro-5-trifluoromethyl-2-pyridyl)pyrazole and 100 ml of trifluoroacetic acid at 20° C. with stirring in the course of 5 minutes and it was stirred at 25° C. for 14 hours. The reaction mixture was poured onto 500 ml of water and extracted 3× with methylene chloride. The organic phase was washed with water, sodium hydrogencarbonate and saturated sodium chloride solution in succession and dried over magnesium sulfate. After concentrating under reduced pressure, stirring with ether/pentane, filtering off with suction and drying, 9.0 g (85% of theory) of 4-nitro-5-propionamido-1-(3-chloro-5-trifluoromethyl-(N-oxido)-2-pyridyl)pyrazole of m.p. 143–146° C. were obtained.

b) 7.2 g (0.019 mol) of N-oxide from a) were added with stirring to 100 ml of phosphorus oxychloride and it was stirred at 100° C. for 3 hours. The reaction mixture was concentrated under reduced pressure and partitioned between ice water and methylene chloride. The aqueous phase was extracted once with methylene chloride. The organic extracts were washed and dried as above and then filtered through active carbon and neutral alumina. After concentrating under reduced pressure, 2.6 g (34.3% of theory) of the title compound were obtained as a viscous resin. This crystallized, after chromatographing with methylene chloride on silica gel and concentrating, with the m.p. 148–154° C. (Active Compound Example No. 9.001).

EXAMPLE 2

4-Nitro-5-N(propargyl)propionamido-1-(3,6-dichloro-5-trifluoromethyl-2-pyridyl)pyrazole 3.2 g (0.008 mol) of the compound from the above example in 50 ml of dimethylformamide were added to a mixture of 0.22 g (0.0088 mol) of 95% strength sodium hydride in 50 ml of dimethylformamide with stirring in the course of 10 minutes. The mixture was stirred at 50° C. for 30 minutes and then 1.05 g (0.0088 mol) of 3-bromopropyne were added at 80° C. in the course of 3 minutes. After stirring at 80° C. for 8 hours, it was cooled and concentrated under reduced pressure. The residue was partitioned between water and methylene chloride, and the organic phase was dried over magnesium sulfate, filtered through silica gel and concentrated. After stirring in ether/pentane, 2.7 g (77.4% of theory) of the title compound of m.p. 107–110° C. were obtained (Active Compound Example No. 9.006).

EXAMPLE 3

5-Amino-4-cyano-1-(3,6-dichloro-5-trifluoromethyl-2-pyridyl)pyrazole 24.6 g (0.1 mol) of 3,6-dichloro-2-hydrazino-5-trifluoromethylpyridine were added to a mixture of 12.2 g (0.1 mol) of ethoxymethylenemalononitrile and 200 ml of ethanol with stirring at 20° C. and it was stirred at 78° C. for 10 hours. After cooling, the reaction mixture was concentrated under reduced pressure and the residue was taken up in methylene chloride. It was extracted 3× with water and the organic phase separated off was dried over magnesium sulfate, filtered off with suction through neutral alumina and then concentrated under reduced pressure. After stirring in ether/pentane, 13.3 g (41.3% of theory) of the title compound of m.p. 168–171° C. were obtained (Active Compound Example No. 2a.002).

EXAMPLE 4

5-Amino-4-cyano-1-(3-chloro-6-methoxy-5-trifluoromethyl-2-pyridyl)pyrazole 5 ml of methanol were added to a suspension of 0.23 g (0.0092 mol) of 95% strength sodium hydride in 75 ml of methyl tert-butyl ether at 20° C. in the course of 10 minutes and the mixture was stirred for 25 minutes to give a clear solution. 3 g (0.0098 mol) of 5-amino-4-cyano-1-(3-chloro-6-fluoro-5-trifluoromethyl-2-pyridyl)pyrazole (Active Compound Example No. 2a.001) in 50 ml of methyl tert-butyl ether were then added with stirring and the mixture was stirred at 25° C. for 2 hours. About 50 g of ice and 100 ml of 1N hydrochloric acid were added and the phases were separated. The organic phase was washed with saturated sodium chloride solution, dried and filtered through silica gel. After concentrating, stirring with ether/pentane, filtering off with suction and drying, 2.4 g (77% of theory) of the title compound of m.p. 135–139° C. were obtained (Active Compound Example No. 2c.001).

EXAMPLE 5

5-Bromo-4-cyano-1-(3,6-dichloro-5-trifluoromethyl-2-pyridyl)pyrazole 10.7 g (0.0667 mol) of bromine were added at 25° C. with stirring in the course of 10 minutes to 9.3 g (0.029 mol) of the compound from Example 3 in 200 ml of chloroform; 4.5 g [0.0435 mol] of tert-butyl nitrite were then added in the course of 5 minutes at the same temperature and the mixture was subsequently stirred for 14 hours. The reaction solution was stirred into 1 l of ice water and then extracted with methylene chloride. The organic extract was washed in the customary manner and dried, filtered off with suction through neutral alumina and concentrated under reduced pressure. After triturating in ether/pentane, filtering off with suction and drying, 4.0 9 (35.7% of theory) of the title compound of m.p. 121–122° C. were obtained (Active Compound Example No. 2a.022).

EXAMPLE 6

Ethyl 5-amino-1-(5-chloro-6-propargyloxy-3-trifluoromethyl-2-pyridyl)pyrazole-4-carboxylate 19.1 g (0.113 mol) of ethoxymethylene cyanoacetate were added to a mixture of 30 g (0.113 mol) of 5-chloro-6-propargyloxy-3-trifluoromethyl-2-pyridylhydrazine and 300 ml of methyl glycol with stirring in the course of 10 minutes and it was stirred at 80° C. for 30 minutes. After stirring at 120° C. for a further 4 hours, the reaction mixture was concentrated under reduced pressure and stirred in ether/pentane. After filtering off with suction, 36.1 g (82.2% of theory) of the title compound of m.p. 118–119° C. were obtained (Active Compound Example No. 9.005).

EXAMPLE 7

5-Allylamino-4-nitro-1-(3-chloro-5-trifluormethyl-2-pyridyl)pyrazole 1.0 g (0.0082 mol) of 3-bromopropene was added with stirring to a mixture of 2.3 g (0.0075 mol) of 5-amino-4-nitro-1-(3-chloro-5-trifluoromethyl-2-pyridyl)pyrazole, 0.6 g (0.0041 mol) of potassium carbonate and 50 ml of dimethylformamide and it was stirred at 100° C. for 2 hours. After cooling, it was concentrated under reduced pressure and the residue was partitioned between water and methylene chloride. The organic phase was dried, filtered off with suction through silica gel and concentrated, 1.6 g (61.3% of theory) of the title compound being obtained as a viscous resin. After chromatographing on silica gel and concentrating, colorless crystals of m.p. 94–95° C. were obtained (Active Compound Example No. 9.003).

EXAMPLE 8

5-Amino-4-thiocyanato-1-(3-chloro-6-fluoro-5-trifluoromethyl-2-pyridyl)pyrazole 3.3 g (0.0335 mol) of potassium thiocyanate were added to a mixture of 4.7 g (0.0168 mol) of 5-amino-(3-chloro-6- fluoro-5-trifluoromethyl-2-pyridyl)pyrazole and 70 ml of conc. acetic acid at 10° C. with stirring in the course of 2 minutes. 2.7 g of bromine in 10 ml of glacial acetic acid were then added in the course of 5 minutes and stirring was continued at 23° C. for 15 minutes. The reaction mixture was added to 300 ml of ice water and the precipitate which was deposited was filtered off with suction, and the solid was taken up in methylene chloride and dried over magnesium sulfate. After filtering off with suction through silica gel, concentrating under reduced pressure, stirring with ether/petroleum ether 1:1, filtering off with suction and drying, 4.2 g (74% of theory) of the title compound of m.p. 109–114° C. were obtained (Active Compound Example No. 6a.001).

EXAMPLE 9

5-Bromo-4-nitro-1-(6-allylamino-3-chloro-5-trifluoromethyl-2-pyridyl)pyrazole 0.3 g (0.00565 mol) of allylamine and 0.6 g (0.00565 mol) of triethylamine were added to a mixture of 2.2 g (0.00565 mol) of 5-bromo-4-nitro-1-(3-chloro-6-fluoro-5-trifluoromethyl-2-pyridyl)pyrazole and 50 ml of tetrahydrofuran at 22° C. with stirring in the course of 5 minutes and the mixture was subsequently stirred for 2½ hours. After working up according to the above example and chromatographing with methylene chloride on silica gel, 0.9 g (37% of theory) of the title compound was obtained as a colorless resin. $^1$H-NMR (CDCL$_3$/TMS) δ (ppm) allyl 3.95 (s/2), 5.05 (tr/2), 5.85 (m/1); NH 7.6 (tr/1); pyrid 8.4 (s/1); pyraz. 8.8 (s/1) (Active Compound Example No. 9.022).

EXAMPLE 10

5-Allylamino-4-nitro-1-[3-fluoro-5-trifluoromethyl-2-pyridyl]pyrazole 0.5 g (0.0085 mol) of allylamine was added to 1.5 g (0.0042 mol) of 5-bromo-4-nitro-1-(3-fluoro-5-trifluoromethyl-2-pyridyl)pyrazole in 50 ml of methyl tert-butyl ether at 22° C. with stirring in the course of 2 minutes and the mixture was then stirred at 50° C. for 2 hours. After cooling, it was diluted with 100 ml of ethyl acetate, extracted with 0.1 N hydrochloric acid, washed with water and with sodium chloride solution, dried and concentrated. After stirring with pentane, 1.1 g of the title compound of m.p. 90–92° C. were obtained (Active Compound Example No. 9.034). The following tables list further compounds I which were prepared in a similar manner to the examples or can be prepared either by the processes described above or by methods known per se.

TABLE 12

| No. | R$^1$ | R$^2$ | R$^3$ | R$^4$ | R$^5$ | R$^6$ | M.p. (° C.), n$^{25}$$_D$, $^1$H-NMR (CDCl$_3$/TMS) δ |
|---|---|---|---|---|---|---|---|
| Ic.001 | H | NO$_2$ | NH$_2$ | OCH$_3$ | CF$_3$ | Cl | 143–145 |
| Ic.021 | H | NO$_2$ | Br | OCH$_3$ | CF$_3$ | Cl | 83–86 |

TABLE 13

| No. | R$^1$ | R$^2$ | R$^3$ | R$^4$ | R$^5$ | R$^6$ | M.p. (° C.), n$^{25}$$_D$, $^1$H-NMR (CDCl$_3$/TMS) δ |
|---|---|---|---|---|---|---|---|
| 2c.001 | H | CN | NH$_2$ | OCH$_3$ | CF$_3$ | Cl | 135–139 |
| 2d.001 | H | CN | NH$_2$ | OCH$_3$ | Cl | CF$_3$ | 163–165 |

TABLE 14

| No. | R$^1$ | R$^2$ | R$^3$ | R$^4$ | R$^5$ | R$^6$ | M.p. (° C.), n$^{23}$$_D$, $^1$H-NMR (CDCl$_3$/TMS) δ |
|---|---|---|---|---|---|---|---|
| 9.001 | H | NO$_2$ | NH—C(=O)—C$_2$H$_5$ | Cl | CF$_3$ | Cl | 148–154 |
| 9.002 | H | NO$_2$ | N(CH$_2$CH=CH$_2$)(C(=O)—C$_2$H$_5$) | H | CF$_3$ | Cl | 81–84 |
| 9.003 | H | NO$_2$ | NHCH$_2$—CH=CH$_2$ | H | CF$_3$ | Cl | 94–95 |
| 9.004 | H | CO$_2$C$_2$H$_5$ | NH$_2$ | OCH$_3$ | Cl | CF$_3$ | 95–98 |
| 9.005 | H | CO$_2$C$_2$H$_5$ | NH$_2$ | OCH$_2$—C≡CH | Cl | CF$_3$ | 118–119 |
| 9.006 | H | NO$_2$ | N(CH$_2$—C≡CH)(C(=O)—C$_2$H$_5$) | Cl | CF$_3$ | Cl | 107–110 |
| 9.007 | H | NO$_2$ | N=CH—N(CH$_3$)$_2$ | H | CF$_3$ | Cl | 119–121 |
| 9.008 | H | CO$_2$C$_2$H$_5$ | NH$_2$ | OCH$_2$—C≡CH | CF$_3$ | Cl | 185–186 |

TABLE 14-continued

| No. | R$^1$ | R$^2$ | R$^3$ | R$^4$ | R$^5$ | R$^6$ | M.p. (° C.), n$^{23}_D$, $^1$H-NMR (CDCl$_3$/TMS) δ |
|---|---|---|---|---|---|---|---|
| 9.009 | H | NO$_2$ | NH—C(=O)—C$_2$H$_5$ | F | CF$_3$ | Cl | 136–138 |
| 9.010 | H | NO$_2$ | NH—CH$_2$—C≡CH | H | CF$_3$ | Cl | 139–142 |
| 9.011 | H | CN | NH$_2$ | OCH$_2$—C≡CH | CF$_3$ | Cl | 194–196 |
| 9.012 | H | CO$_2$C$_2$H$_5$ | NH$_2$ | OCH$_3$ | CF$_3$ | Cl | 165–166 |
| 9.013 | H | CO$_2$C$_2$H$_5$ | Br | OCH$_2$C≡CH | CF$_3$ | Cl | n$^{23}_D$ = 1.5440 |
| 9.014 | H | NO$_2$ | NH$_2$ | OCH$_2$C≡CH | CF$_3$ | Cl | 208–210 |
| 9.015 | H | NO$_2$ | NH—C(=O)—C$_2$H$_5$ | OCH$_3$ | CF$_3$ | Cl | 127–128 |
| 9.016 | H | CN | NH$_2$ | OCH(CH$_3$)CO$_2$C$_2$H$_5$ | CF$_3$ | Cl | 175–177 |
| 9.017 | H | CO$_2$C$_2$H$_5$ | NH$_2$ | OCH$_2$CO$_2$CH$_3$ | CF$_3$ | Cl | 129–131 |
| 9.018 | H | CO$_2$C$_2$H$_5$ | NH$_2$ | OCH(CH$_3$)CO$_2$C$_2$H$_5$ | CF$_3$ | Cl | 114–118 |
| 9.019 | H | CN | NH$_2$ | OCH—C≡CH | Cl | CF$_3$ | 180–182 |
| 9.020 | H | NO$_2$ | NH—C(=O)—CH$_3$ | OH | CF$_3$ | Cl | 220–224 |
| 9.021 | H | NO$_2$ | NH$_2$ | OH | CF$_3$ | Cl | 73–75 |
| 9.022 | H | NO$_2$ | Br | NHCH$_2$—CH=CH$_2$ | CF$_3$ | Cl | Resin, pyraz. 8,8, s/1, pyrid. 8,4, s/1 |
| 9.023 | H | NO$_2$ | NH—C(=O)—C$_2$H$_5$ | H | CF$_3$ | F | 101–103 |
| 9.024 | CH$_3$ | NO$_2$ | CH$_3$ | Cl | CF$_3$ | Cl | 120–123 |
| 9.025 | CH$_3$ | NO$_2$ | CH$_3$ | Cl | CF$_3$ | Cl | 123–124 |
| 9.026 | H | NO$_2$ | NH$_2$ | H | CF$_3$ | F | 168–169 |
| 9.027 | H | CN | NH$_2$ | H | CF$_3$ | F | 241–242 |
| 9.028 | H | CO$_2$Et | NH$_2$ | H | CF$_3$ | F | 110–113 |
| 9.029 | H | CN | N[C(=O)—CH$_3$]$_2$ | F | CF$_3$ | Cl | 146–150 |
| 9.030 | H | SCN | N[C(=O)—CH$_3$]$_2$ | F | CF$_3$ | Cl | 135–136 |
| 9.031 | H | NO$_2$ | Br | H | CF$_3$ | F | 1.5520 |
| 9.032 | H | NO$_2$ | NHCH$_3$ | H | CF$_3$ | F | 114–115 |
| 9.033 | H | NO$_2$ | NHet | H | CF$_3$ | F | 141–143 |
| 9.034 | H | NO$_2$ | NH—CH$_2$—CH=CH$_2$ | H | CF$_3$ | F | 90–92 |
| 9.035 | H | NO$_2$ | NH—CH$_2$—C≡CH | H | CF$_3$ | F | 163–165 |
| 9.036 | H | CN | Br | Br\C=C/Br, O—CH$_2$, H | Cl | CF$_3$ | 113–115 |
| 9.037 | H | CN | Br | H | CF$_3$ | F | 91–92 |
| 9.038 | H | CN | Br | H | CF$_3$ | F | 170–173 N-Oxide |
| 9.039 | H | CN | NH$_2$ | O-et | CF$_3$ | Cl | 179–180 |
| 9.040 | H | CN | NH$_2$ | O-i-C$_3$H$_7$ | CF$_3$ | Cl | 182–183 |

The compounds I and the herbicidal compositions containing them and their environmentally tolerable salts, eg. of alkali metals, alkaline earth metals or ammonia and amines, and the herbicidal compositions thus containing them can highly effectively control broad-leaved weeds and grass weeds in crops such as wheat, rice, maize, soybeans and cotton without harming the crop plants, an effect which occurs especially even at low application rates.

In consideration of the versatility of the application methods, the compounds I or compositions containing them can additionally be employed in a further number of crop plants for the elimination of undesired plants. Suitable crops, for example, are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, vicia faba, Vitis vinifera, Zea mays.*

Moreover, the compounds I can also be used in crops which have been made largely tolerant to the action of I or other herbicides by breeding and/or by means of genetic engineering methods.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The compounds I and the herbicidal compositions containing them can be applied by spraying, atomizing, dusting, scattering or watering, for example in the form of directly sprayable aqueous solutions, powders, suspensions, even high-percentage aqueous, oily or other suspensions or dispersions, emulsions, oil dispersions, pastes, dusting compositions, scattering compositions or granules. The application forms depend on the intended uses; in each case they should if possible ensure the finest dispersion of the active compounds according to the invention.

Suitable inert additives are mineral oil fractions of medium to high boiling point, such as kerosene or diesel oil, further, coal tar oils and oils of vegetable or animal origin, aliphatic, cyclic and aromatic hydrocarbons, eg. paraffins, tetrahydronaphthalene, alkylated naphthalenes or their derivatives, alkylated benzenes and their derivatives, alcohols such as methanol, ethanol, propanol, butanol and cyclohexanol, ketones such as cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substances can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Suitable surface-active substances are the alkali metal, alkaline earth metal or ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols, and also of fatty alcohol glycol ether, condensation products of sulfonated naphthalene and its derivatives with formaldehyde, condensation products of naphthalene or of the naphthalenesulfonic acids with phenol and formaldehyde, polyoxyethylene octylphenyl ethers, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules, can be prepared by binding of the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as grain flour, tree bark, wood and nutshell meal, cellulose powder or other solid carriers.

The formulations in general contain from 0.01 to 95% by weight, preferably from 0.5 to 90% by weight, of active compound. The active compounds are employed here in a purity of from 90 to 100%, preferably 95 to 100% (according to NMR spectrum).

The compounds I according to the invention can be formulated, for example, as follows:

I. 20 parts by weight of the compound No. 9.001 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 9.005 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 9.006 are dissolved in a mixture which consists of 25 parts by weight of cyclohexanone, 65 parts by weight of a mineral oil fraction of boiling point from 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 9.007 are well mixed with 3 parts by weight of the sodium salt of diisobutylnaphthalene-a-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 9.008 are mixed with 97 parts by weight of finely divided kaolin. In this manner, a dusting composition is obtained which contains 3% by weight of the active compound.

VI. 20 parts by weight of the active compound No. 9.009 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

To widen the spectrum of action and to achieve synergistic effects, the 1-(pyridyl)pyrazoles I can be mixed and applied together with numerous representatives of other herbicidal or growth-regulating active compound groups. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1, 3-dione derivatives which carry eg. a carboxyl or carbimino group in the 2-position, quinolinecarboxylic acid derivatives, imidazolinones, sulfonamides, sulfonylureas, aryloxy- or heteroaryloxyphenoxypropionic acids and their salts, esters and amides and others.

Additionally, it may be useful to apply the compounds I on their own or jointly in combination with other herbicides additionally mixed with further crop protection agents, for example with agents for controlling pests or phytopathogenic fungi or bacteria. Further of interest is the miscibility with mineral salt solutions, which are employed for the elimination of nutritional and trace element deficiencies. Nonphytotoxic oils and oil concentrates can also be added.

Depending on the aim of control, time of year, target plants and stage of growth, the application rates of active compound are from 0.001 to 3.0, preferably from 0.01 to 1.0, kg/ha of active substance (a.s.).

USE EXAMPLES

It was possible to show the herbicidal action of the 1-(pyridyl)pyrazoles of the formula I by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth and then covered with transparent plastic hoods until the plants had taken root. This covering caused uniform germination of the test plants if this had not been adversely affected by the active compounds.

For the purposes of post-emergence application, the test plants, depending on growth form, were first raised to a growth height of from 3 to 15 cm and only then treated with the active compounds suspended or emulsified in water. For this purpose, the test plants were either sown directly and grown in the same containers or they were first raised separately as seedlings and transplanted into the test containers a few days before treatment. The application rate for post-emergence treatment was 0.0312 or 0.0156 kg/ha of a.s.

The plants were kept species-specifically at from 10 to 25° C. or 20 to 35° C. The test period extended over 2 to 4 weeks. During this time, the plants were tended and their reaction to the individual treatments was assessed.

Assessment was carried out on a scale of from 0 to 100. 100 here means no emergence of the plants or complete destruction of at least the above-ground parts and 0 means no damage or normal course of growth.

The plants used in the greenhouse tests were made up of the following species:

| Botanical Name | Common Name |
|---|---|
| Abutilon theophrasti | velvet leaf |
| Oryza sativa | rice |
| Solanum nigrum | black nightshade |

COMPARISON EXAMPLE

According to the methods described above, the compound according to the invention and the known comparison composition were employed in the greenhouse post-emergence.

The comparison composition used is:

A From DE 3 520 330

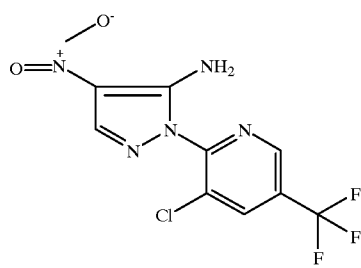

TABLE 15

Comparison of results from greenhouse tests post-emergence

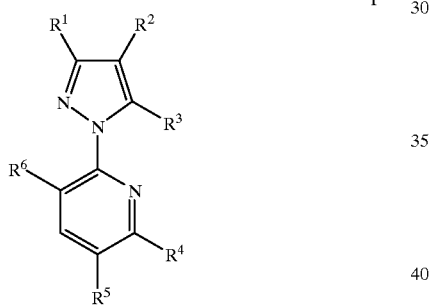

| | Ex. No. | | | |
|---|---|---|---|---|
| | 9.003 | | A | |
| | R | | | |
| | CH$_2$CHCH$_2$ | | H | |
| Application rate (kg/ha of a.s.) | 0.0312 | 0.0156 | 0.0312 | 0.0156 |
| Test plants | damage in % | | | |
| ORYSA | 10 | 0 | 50 | 40 |
| ABUTH | 100 | 70 | 100 | 100 |
| SOLNI | 100 | 100 | 100 | 100 |

We claim:

1. A 1-(pyridyl)pyrazole of the general formula I where the substituents have the following meanings:

$R^1$ is hydrogen, $C_1$–$C_3$-alkyl, halogen, $C_1$–$C_3$-haloalkyl;

$R^2$ is $C_1$–$C_4$-alkyl, $C_2$–$C_4$-alkenyl, $C_2$–$C_4$-alkynyl, $C_1$–$C_4$-alkoxy, $C_3$–$C_4$-alkenyloxy, $C_3$–$C_4$-alkynyloxy, each of which can be substituted by 1–6 halogen atoms, NO$_2$, cyano, halogen, thiocyanato, amino, or further a radical NH—C(=O)R$^9$;

$R^3$ is amino, halogen, thiocyanato, cyano, nitro, hydroxyl, $C_1$–$C_3$-alkyl, $C_1$–$C_3$-haloalkyl, or further a radical S(O)$_n$R$^8$, N(R$^{10}$)R$^{11}$, OR$^{12}$, SR$^{13}$, N=C(R$^{14}$)—N(R$^{15}$)R$^{16}$ or, if R$^1$=hydrogen, additionally N=C(R$^{11}$)R$^{18}$;

$R^4$ is halogen, a radical XR$^{19}$;

$R^5$ and $R^6$ independently of one another are halogen or $C_1$–$C_3$-haloalkyl;

$R^7$ is hydrogen, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy-$C_2$–$C_4$-alkyl, $C_3$–$C_6$-cycloalkyl, $C_1$–$C_4$-alkoxy, $C_1$–$C_4$-alkylamino or $C_1$–$C_4$-dialkylamino;

$R^8$ is $C_1$–$C_4$-alkyl, $C_1$–$C_4$-haloalkyl, $C_1$–$C_4$-alkoxy, chlorine, amino or $C_1$–$C_4$-alkylamino;

$R^9$ is $C_1$–$C_4$-alkyl, $C_1$–$C_4$-haloalkyl, $C_1$–$C_4$-alkoxy-$C_1$–$C_4$-alkyl, $C_2$–$C_4$-alkenyl, $C_2$–$C_4$-alkynyl or $C_1$–$C_4$-alkoxy;

$R^{10}$ is hydrogen, $C_1$–$C_4$-alkyl or a radical C(=O)R$^7$;

$R^{11}$ is hydrogen, $C_1$–$C_4$-alkyl, $C_3$–$C_4$-alkenyl, $C_3$–$C_4$-alkynyl, a radical C(=O)R$^7$ or S(O)$_n$R$^8$;

$R^{12}$ is $C_1$–$C_3$-alkoxy, $C_1$–$C_3$-haloalkoxy, $C_2$–$C_4$-alkenyloxy, $C_3$–$C_4$-alkynyloxy, $C_1$–$C_5$-alkoxycarbonyl-$C_1$–$C_4$-alkyl or $C_1$–$C_4$-alkoxy-$C_2$–$C_4$-alkoxycarbonyl-$C_1$–$C_6$-alkyl;

$R^{13}$ is $C_1$–$C_4$-alkoxycarbonyl-$C_1$–$C_4$-alkyl or $C_1$–$C_4$-alkoxy-$C_2$–$C_4$-alkoxycarbonyl-$C_1$–$C_6$-alkyl;

$R^{14}$ is hydrogen or $C_1$–$C_3$-alkyl;

$R^{15}$ is $C_1$–$C_4$-alkyl;

$R^{16}$ and $R^{17}$ independently of one another are hydrogen or $C_1$–$C_4$-alkyl;

$R^{18}$ is hydrogen, $C_1$–$C_4$-alkyl, $C_1$–$C_4$-haloalkyl, $C_1$–$C_3$-alkoxy-$C_1$–$C_3$-alkyl, $C_3$–$C_6$-cycloalkyl, $C_2$–$C_4$-alkenyl or $C_2$–$C_4$-alkynyl and $R^{19}$ is hydrogen, $C_1$–$C_6$-alkyl, $C_2$–$C_6$-alkenyl or $C_2$–$C_6$-alkynyl, where these groups can carry up to 6 halogen atoms, $C_3$–$C_6$-cycloalkyl which for its part can carry up to three $C_1$–$C_3$-alkyl radicals or up to 5 halogen atoms, $C_1$–$C_6$-cyanoalkyl, $C_1$–$C_4$-alkoxy-$C_2$–$C_4$-alkyl, 3-oxetanyl, carboxyl-$C_1$–$C_6$-alkyl, $C_1$–$C_4$-alkoxycarbonyl-$C_1$–$C_6$-alkyl, $C_1$–$C_4$-alkoxy-$C_2$–$C_4$-alkoxycarbonyl-$C_1$–$C_6$-alkyl, $C_1$–$C_4$-alkylaminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-(α-alkylalkyliden)iminoxy-$C_2$–$C_6$-alkyl, cyclopropylmethyl, or, if X=O, additionally $C_1$–$C_4$-alkylamino, $C_1$–$C_4$-dialkylamino, $C_1$–$C_6$-alkylidenimino or α-($C_1$–$C_4$-alkyl)-$C_2$–$C_6$-alkylidenimino;

x is oxygen, sulfur, S=O or SO$_2$;

halogen is fluorine, chlorine, bromine or iodine and n is 0, 1 or 2, and the N-oxides and the agriculturally utilizable salts of the compounds I, with the exception of 5-amino-1-(3,6-dichloro-5-trifluoromethyl-2-pyridyl)-4-cyanopyrazole.

2. A 1-(pyridyl)pyrazole of the formula I as defined in claim 1, where $R^1$ is hydrogen;

$R^2$ is alkoxy, $C_1$–$C_4$-haloalkoxy, NO$_2$, cyano, halogen, thiocyanato, amino, C(=O)R$^7$, S(O)$_n$RB or NH—C(=O)R$^9$;

$R^3$ is amino, halogen, thiocyanato, cyano, nitro, hydroxyl, $C_1$–$C_3$-alkyl, $C_1$–$C_3$-haloalkyl, S(O)$_n$R$^8$, N(R$^{10}$)R$^{11}$, OR$^{12}$, SR$^{13}$, N=C(R$^{14}$)—N(R$^{15}$)R$^{16}$ or, if R$^1$=hydrogen, additionally N=C(R$^{17}$)R$^{18}$;

$R^4$ is halogen, a radical XR$^{19}$;

$R^5$ and $R^6$ independently of one another are halogen or trifluoromethyl;

$R^7$ is $C_1$–$C_4$-alkyl, $C_1$–$C_4$-haloalkyl, $C_1$–$C_4$-alkoxy or $C_1$–$C_4$-alkylamino;

$R^8$ is $C_1$–$C_4$-alkyl, trifluoromethyl, $C_1$–$C_4$-alkoxy, chlorine, amino, methylamino or ethylamino;

$R^9$ is $C_1$–$C_4$-alkyl, $C_1$–$C_4$-haloalkyl or $C_1$–$C_4$-alkoxy;

$R^{10}$ is hydrogen, $C_1$–$C_4$-alkyl or C(=O)R$^7$;

$R^{11}$ is $C_1$–$C_4$-alkyl, $C_3$–$C_4$-alkenyl, $C_3$–$C_4$-alkynyl, C(=O)R$^7$ or S(O)$_n$R$^8$;

$R^{12}$ is $C_1$–$C_3$-alkoxy, $C_1$–$C_3$-haloalkoxy, $C_3$–$C_4$-alkenyl, $C_3$–$C_4$-alkynyl or $C_1$–$C_5$-alkoxycarbonyl-$C_1$–$C_4$-alkyl;

$R^{13}$ is $C_1$–$C_4$-alkoxycarbonyl-$C_1$–$C_4$-alkyl;

$R^{14}$, $R^{16}$, and $R^{17}$ are hydrogen or $C_1$–$C_3$-alkyl;

$R^{15}$ is $C_1$–$C_4$-alkyl;

$R^{18}$ is $C_1$–$C_4$-alkyl, $C_1$–$C_4$-haloalkyl or $C_2$–$C_4$-alkenyl;

$R^{19}$ is $C_1$–$C_4$-alkyl, $C_3$–$C_4$-alkenyl, $C_3$–$C_4$-alkynyl, $C_1$–$C_4$-haloalkyl, $C_1$–$C_4$-cyanoalkyl, $C_1$–$C_4$-alkoxycarbonyl-$C_1$–$C_4$-alkyl, or, if X=O, additionally $C_1$–$C_4$-alkylamino or $C_1$–$C_4$-alkylidenimino;

X is oxygen or sulfur;

halogen is fluorine or chlorine and n is 0, 1 or 2.

3. A herbicidal composition comprising a herbicidally active amount of at least 1-(pyridyl)pyrazole of the formula I or an agriculturally utilizable salt of I as defined in claim 1, and at least one inert liquid and/or solid carrier and also, if desired, at least one adjuvant.

4. A process for the production of herbicidally active compositions, which comprises mixing a herbicidally active amount of at least one 1-(pyridyl)pyrazole of the formula I or an agriculturally utilizable salt of I as defined in claim 1, and at least one inert liquid and/or solid carrier and also, if desired, at least one adjuvant.

5. A process for the production of compositions having desiccant and/or defoliant activity, which comprises mixing an amount having desiccant and/or defoliant activity of at least one 1-(pyridyl)pyrazole of the formula I or an agriculturally utilizable salt of I as defined in claim 1, and at least one inert liquid and/or solid carrier and also, if desired, at least one adjuvant.

6. A process for controlling undesired vegetation, which comprises allowing a herbicidally active amount of at least one substituted 1-(pyridyl)pyrazole of the formula I or of an agriculturally utilizable salt of I as defined in claim 1 to act on plants, their habitat or on seed.

* * * * *

UNITED STATES PATENT AND TRADEMARK OFFICE
CERTIFICATE OF CORRECTION

PATENT NO.   : 6,107,253
DATED        : August 22, 2000
INVENTOR(S)  : Hamprecht et al.

Page 1 of 1

It is certified that error appears in the above-identified patent and that said Letters Patent is hereby corrected as shown below:

<u>Column 55,</u>
Line 54, "$N=C(R^{11})R^{18}$;" should be -- $N=C(R^{17})R^{18}$; --.

Signed and Sealed this

Fourteenth Day of August, 2001

*Attest:*

*Attesting Officer*

NICHOLAS P. GODICI
*Acting Director of the United States Patent and Trademark Office*